(12) United States Patent
Feldsine et al.

(10) Patent No.: US 7,030,403 B2
(45) Date of Patent: Apr. 18, 2006

(54) SAMPLE COLLECTION AND BIOLUMINESCENT SAMPLE TESTING SYSTEM

(75) Inventors: Philip T. Feldsine, Mercer Island, WA (US); Tim A. Kelly, Bellevue, WA (US); Jim Christensen, Portland, OR (US); Joseph B. Di Carlo, Long Beach, CA (US); Mark Andersen, Pasadena, CA (US); Anita Kressner, Bellevue, WA (US)

(73) Assignee: Biocontrol Systems, Inc., Bellevue, WA (US)

( * ) Notice: Subject to any disclaimer, the term of this patent is extended or adjusted under 35 U.S.C. 154(b) by 384 days.

(21) Appl. No.: 10/313,941

(22) Filed: Dec. 5, 2002

(65) Prior Publication Data

US 2003/0143752 A1    Jul. 31, 2003

Related U.S. Application Data

(60) Provisional application No. 60/338,844, filed on Dec. 6, 2001.

(51) Int. Cl.
*G01N 15/06* (2006.01)

(52) U.S. Cl. ................ 250/573; 250/239

(58) Field of Classification Search ............ 250/573, 250/576, 239, 214.1; 422/52, 82.08; 435/287.2, 435/287.6; 436/165, 172, 287.4, 287.6
See application file for complete search history.

(56) References Cited

U.S. PATENT DOCUMENTS

| | | | |
|---|---|---|---|
| 3,640,267 A | 2/1972 | Hurtig et al. | 128/2 |
| 4,039,259 A | 8/1977 | Saito et al. | 356/53 |
| 4,112,070 A | 9/1978 | Harmening | 424/101 |
| 4,150,950 A | 4/1979 | Takeguchi et al. | 23/230 B |
| 4,213,703 A | 7/1980 | Haunold et al. | 356/244 |
| 4,353,868 A | 10/1982 | Joslin et al. | 422/101 |
| 4,409,988 A | 10/1983 | Greenspan | 128/759 |
| 4,586,818 A | 5/1986 | Lohr | 356/244 |
| 4,604,360 A | 8/1986 | Hounsell | 435/287 |
| 4,653,510 A | 3/1987 | Koll | 128/756 |
| 4,685,059 A | 8/1987 | Yamamoto | 364/415 |
| 4,707,450 A | 11/1987 | Nason | 435/295 |
| 4,730,933 A | 3/1988 | Lohr | 356/440 |
| 4,755,055 A | 7/1988 | Johnson et al. | 356/440 |

(Continued)

FOREIGN PATENT DOCUMENTS

EP          0 717 840 B1      11/1998

(Continued)

OTHER PUBLICATIONS

BioControl® Systems Inc., "Lightning™—System Guide.".

(Continued)

*Primary Examiner*—Que T. Le
(74) *Attorney, Agent, or Firm*—Seed IP Law Group PLLC

(57) ABSTRACT

Methods and apparatus for evaluating the quality of a sample of a product, an ingredient, an environment or process by measuring multiple parameters thereof, including light emitted from a reacting sample containing ATP, ADP, alkaline phosphatase or other parameters such as pH, temperature, conductivity, reduction potential, dissolved gases, specific ions, and microbiological count. The apparatus comprises an integrated sample testing device used to collect a sample, mix reagents, react the sample, and collect it in a measurement chamber. The apparatus also comprises an instrument having a photon detection assembly for use with the sample testing device. The instrument can also comprise one or more sensing probes and a communication port to facilitate data collection, transfer and analysis.

61 Claims, 15 Drawing Sheets

U.S. PATENT DOCUMENTS

| | | | | |
|---|---|---|---|---|
| 4,770,853 | A | 9/1988 | Bernstein | 422/58 |
| 4,813,432 | A | 3/1989 | Saint-Amand | 128/749 |
| 4,978,504 | A | 12/1990 | Nason | 422/61 |
| 5,043,141 | A | 8/1991 | Wilson et al. | 422/52 |
| 5,086,233 | A | 2/1992 | Stafford et al. | 250/576 |
| 5,100,028 | A | 3/1992 | Seifert | 222/107 |
| 5,108,175 | A | 4/1992 | Whitlock | 356/218 |
| 5,139,745 | A | 8/1992 | Barr et al. | 422/82.05 |
| 5,238,649 | A | 8/1993 | Nason | 422/58 |
| 5,266,266 | A | 11/1993 | Nason | 422/58 |
| 5,558,986 | A | 9/1996 | Lundin | 435/4 |
| 5,624,810 | A | 4/1997 | Miller et al. | 435/8 |
| 5,624,815 | A | 4/1997 | Grant et al. | 435/30 |
| 5,637,874 | A * | 6/1997 | Honzawa et al. | 250/361 C |
| 5,783,399 | A | 7/1998 | Childs et al. | 435/7.2 |
| 5,827,675 | A | 10/1998 | Skiffington et al. | 435/8 |
| 5,905,029 | A | 5/1999 | Andreotti et al. | 435/8 |
| 5,916,802 | A | 6/1999 | Andreotti | 435/287.7 |
| 5,917,592 | A | 6/1999 | Skiffington | 356/244 |
| 5,918,259 | A | 6/1999 | Squirrell | 73/28.01 |
| 5,919,647 | A | 7/1999 | Hiramatsu et al. | 435/29 |
| 5,962,247 | A | 10/1999 | Foote et al. | 435/21 |
| 5,965,453 | A | 10/1999 | Skiffington et al. | 436/165 |
| 6,043,047 | A | 3/2000 | Foote et al. | 435/21 |
| 6,055,050 | A | 4/2000 | Skiffington | 356/244 |
| 6,180,395 | B1 | 1/2001 | Skiffington et al. | 435/287.6 |
| 6,218,176 | B1 | 4/2001 | Berthold et al. | 435/287.9 |
| 2004/0030535 | A1 | 2/2004 | Johnson et al. | 702/189 |

FOREIGN PATENT DOCUMENTS

| | | |
|---|---|---|
| EP | 1 028 312 A1 | 8/2000 |
| WO | WO 95/07457 | 3/1995 |
| WO | WO 95/25948 | 9/1995 |
| WO | WO 97/23596 | 7/1997 |
| WO | WO 99/19709 | 4/1999 |
| WO | WO 99/31218 | 6/1999 |
| WO | WO 00/36139 | 6/2000 |
| WO | WO 00/40748 | 7/2000 |
| WO | WO 00/42419 | 7/2000 |
| WO | WO 01/38846 A1 | 5/2001 |
| WO | WO 03/050513 A2 | 6/2003 |

OTHER PUBLICATIONS

IDEXX Laboratories, Inc., "Lightning® Index™ Proficiency Program," prior to Feb. 2000.

IDEXX Food Safety Net Services, Inc., "Lightning Index™ Reports," prior to Feb. 2000.

BioControl® Systems Inc., Example Spreadsheet, 2000.

BioControl® Systems Inc., "Lightning®—Installation Guide," 2000.

"Trust to Lightning," International Food Hygiene, vol. 10, No. 8, Mar. 2000.

"Leading Portable Monitor," International Food Hygiene, vol. 10, No. 7, Jan./Feb. 2000.

* cited by examiner

SAMPLE COLLECTION AND BIOLUMINESCENT SAMPLE TESTING SYSTEM

BACKGROUND OF THE INVENTION

1. Field of the Invention

The disclosure is related to the field of environmental testing, for example, the testing of food, and of materials and surfaces with which food comes into contact.

2. Description of the Related Art

Safety in the food, pharmaceutical and cosmetic reference industries, in terms of contamination control and hygiene, utilizing HACCP (Hazard Analysis and Critical Control Point) principles, is of growing concern, not only to control the occurrence of pathogenic microorganisms, but also in preventing hazards before they become widespread and expensive problems. HACCP is the science-based system accepted internationally for ensuring food safety. HACCP has been adopted by the FDA and USDA as well as by other countries. It has been endorsed by the National Academy of Sciences, the Codex Alimentarius Commission (an international food standard-setting organization), and the National Advisory Committee on Microbiological Criteria for Foods. Developed nearly 30 years ago for the space program, HACCP has proven to be effective to ensure that food safety hazards are controlled to prevent unsafe food from reaching the consumer.

In the United States alone, since 1995, HACCP based systems have been mandated for the following industries by the Federal Government:

Seafood—(21 C.F.R. Parts 123 and 1240 Procedures for the Safe and Sanitary Processing and Importing of Fish and Fishery Products; Final Rule) in December, 1995

Meat and Poultry—(9 C.F.R. Part 304, et al, Pathogen Reduction: Hazard Analysis and Critical Control Point (HACCP) Systems; Final Rule) in July, 1996

Fruit and Vegetable Juice—(21 CFR Part 120: Hazard Analysis and Critical Control Point (HACCP); Procedures for the Safe and Sanitary Processing and importing of Juice; Final Rule) in January, 2001

Adoption of HACCP will continue to increase for the foreseeable future. The FDA has published an Advance Notice of Proposed Rule Making (ANPRM) for HACCP to be applied for the rest of the food industry including both domestic and imported food products. Also, in January 2000, the National Conference on Interstate Milk Shipments (NCIMS) recommended the use of a voluntary HACCP Pilot Program as an alternative to the traditional inspection system for Grade A Dairy products.

In order for a food manufacturer to effectively comply with HACCP based requirements or standards, it is vital that it have an effective system in place to collect, monitor, and analyze relevant HACCP data. The necessity for this can be seen by examining the seven (7) HACCP principles that a food manufacturer has to follow:

1. Conduct a hazard analysis.
2. Determine the critical control points (CCP). A CCP is a point, step or procedure in a food process where a number of possible measurement controls can be applied and, as a result, a food safety hazard can be prevented, eliminated, or reduced to acceptable levels.
3. Establish measurement parameters and critical limits for each CCP and identify methods for measuring the CCP. For example, compliance with a cooking CCP may be assessed by the combination of two indicators: time and temperature.
4. Monitor the CCP to ensure on-going compliance with established critical limits. A monitoring system should not only detect individual deviations, but also analyze data to identify patterns of deviation that could indicate a need to reassess the HACCP plan.
5. Establish corrective actions to be taken when monitoring of important parameters shows that a critical limit has not been met.
6. Maintain accurate records. Effective record keeping is a requirement. HACCP records must be created at the time events occur and include the parameter measurement, date, time and the plant employee making the entry.
7. Verify that the system is working properly initially as well as ongoing. These activities include calibration of the monitoring equipment, direct observations of the monitoring activities and a review of the records.

One essential characteristic of the HACCP system that differentiates it from previous inspection system(s) is that it places responsibility directly on the food manufacturer to ensure food safety. Each processor must be able to identify CCPs, measure a variety of parametric indicators for each CCP (e.g. time and temperature measurements to verify a cooking process), identify deviations, perform trend analysis of deviations, and document the data to show compliance with the HACCP requirements. Currently, there is no one single instrument or analysis procedure available that can perform these critical and essential functions. For example, a food processor is likely to use many single-function monitors to take isolated measurements (e.g. a temperature probe and photometer, both instruments being capable of measuring parameters related to food safety, as discussed further below) and then to enter the readings manually on different data collection sheets. Such collection procedures are tedious and highly subject to human error. In addition, examination of the relationship of multiple parameters to the quality of the production environment is difficult if not nearly impossible. There is a need for a simple and efficient way to collect, store, integrate, and analyze selected CCP in a format that can be directly used to comply with HACCP based requirements and standards.

It is not surprising that the growing reach of HACCP based monitoring programs is progressing concurrently with a trend toward methods of testing that are improved by being more rapid, more sensitive and easier to perform. More stringent standards, such as those associated with HACCP based programs, are expected to motivate such improvements in methods of testing. The reverse is also true in that as test methods improve, standards are likely to become more stringent since compliance can be more accurately, precisely, and efficiently maintained and verified.

This trend toward improved testing of the manufacturing environment is occurring in a wide variety of industries, including, but not limited to, those industries related to food, pharmaceuticals, cosmetics, and medical areas. In such industries, many techniques are used to monitor levels of environmental quality including techniques that use microbiological cultures. Microbiological cultures are a most widely conducted test method, but due to their low-test throughput capacity and long incubation time periods, are of limited use. They cannot measure the quality of the environment immediately prior to commencement of an operation. A variety of tests have been developed which detect and in some cases quantify specific pathogens. They can range from high-throughput automated systems to single-sample test devices. These methods require the growth of microorganisms for detection, which consumes considerable time.

Some techniques such as adenosine triphosphate (ATP) and alkaline phosphatase (AP) measure parameters that indirectly correlate to the level of environmental contamination. Still others monitor factors related to risk of the presence and propagation of microorganisms, i.e. temperature, pH, conductivity, reduction potential, dissolved gases, total solids and protein residues. The latter types of methods approach real-time in their determinations, offering a distinct advantage for the user in obtaining critical environmental quality information on an immediate basis.

Typically, ATP and AP and similar targets of detection use bioluminescent techniques. The protocol involves using a device to collect a sample from a surface of interest, and activation of the device to mix reagents together with the sample to produce light proportional to the amount of ATP/AP sampled. The reaction is then read by inserting the device into a photon-measuring instrument.

One bioluminescent ATP monitoring system is the LIGHTNING system developed by IDEXX LABORATORIES. The device contains a pre-moistened swab, buffer in a bulb at one end and lyophilized reagent in a foil sealed compartment at the reading end. The swab is removed from the device, used to collect a sample from a test surface, and returned to the tube of the device. The bulb is then bent to break open a snap valve, which releases the buffer into the reading chamber when the bulb is squeezed. The sample containing swab is then pushed through a foil barrier, the device is shaken and the reaction proceeds between ATP on the swab and the dissolved (in the buffer) reagent. The device is inserted into the reading chamber of the photon measuring instrument and a reading is taken over a ten-second integration period. The intensity of the bioluminescent signal is proportional to ATP on the swab.

Another system presently in use is called the CHARM SCIENCES POCKETSWAB PLUS. It is an integrated device used with a LUMINATOR T or a Firefly portable luminometer. The device contains a pre-moistened swab. It is removed from the device base, used to swab a surface, returned to the base, then activated by screwing the top portion relative to the base. This action causes the swab tip to puncture separation barriers allowing separate reagents to migrate to the bottom chamber of the base, mixing and reacting with the sample collected on the swab. Shaking is required to facilitate reagent transfer to the bottom and mixing in the bottom chamber.

The activated device is then inserted into a hole in the top of the luminometer and pushed down until it meets a stop. This process displaces a door. The upper portion of the device remains exterior to the instrument, but forms a seal with the reading chamber orifice. A read button in the instrument is then pressed to initiate a signal integration period before a reading is displayed in relative light units (RLU).

Another such system is the BIOTRACE CLEAN-TRACE RAPID CLEANLINESS TEST self-contained device for use with the UNI-LITE XCEL portable luminometer. It also has a pre-moistened swab, which is removed, a sample is collected, and the swab returned. Activation involves forcing the top portion of the device, which contains the sample, down into the base, through membrane-barriers. The swab engages a piercing tip, which breaks the membranes and allows the reagents to mix in a manner similar to that of the CHARM device. Shaking is required to transfer all of the solution to the bottom.

The BIOTRACE luminometer has a cap, which lifts and swivels out of the way to expose the reading chamber. The sample-containing device is lowered into the chamber and the cap is closed. Full closure of the cap opens a light blocking member to allow signal measurement. Like the CHARM unit, a button begins the read cycle, which ends with the light reading display in RLUs.

MERCK also offers a hygiene monitoring system for ATP that utilizes the HY-LITE Monitor along with HY-LITE test swabs, rinse tubes and sampling pens. The swab is moistened in the rinse tube. A surface is swabbed. The swab is returned to the tube and rotated for several seconds to release any collected ATP. The swab is squeezed out and removed. Then the pen is inserted for one second to pick up the sample. The tip of the pen is struck on a hard pad to engage the cuvette. A button is pushed to release the reagents and initiate the reaction in the cuvette. The cuvette is then removed and shaken, it is inserted into the monitor's reading chamber, and a button is pressed to initiate a ten second light integration period. RLUs are then displayed on the monitor screen. A similar system has been developed by CELSIS also know as Hygenia called the SYSTEMSURE portable hygiene monitoring system. The test sequence is similar to that of the MERCK system where the swab is moistened and the surface is swabbed. The reagent is then pipetted into the cuvette. The swab is inserted into the cuvette and rotated for several seconds then removed. The cuvette is capped and inserted into the luminometer, where the reading is initiated.

There is a need for an improved method and apparatus that is designed to enhance ease of use, and improve measurement accuracy and precision. The current systems incorporate unnecessary actions by the operators that are burdensome with respect to certain steps such as pre-moistening, pipetting, rotating, two-handed screwing, two-handed pushing, striking, shaking, and precise timing, which do not adequately control device activation and contribute to increased reading variances.

The present invention provides multiple embodiments of methods and apparatus to overcome several of the aforementioned limitations of existing systems.

BRIEF SUMMARY OF THE INVENTION

This invention is directed toward various embodiments of a monitoring assembly. The assembly comprises an instrument and probe assembly, or sample testing device, that can be used together to efficiently, accurately, and precisely measure a number of different parameters of a sample for monitoring a process or environment, including luminescence parameters. In one embodiment, the instrument comprises a photon detection assembly and the probe assembly is an integrated, self-contained, test device, for sample collection and luminescence reading with the photon detection assembly. Various embodiments of methods for employing the embodiments of the instrument and probe assembly are also a subject of the present invention.

The instrument can operate as a luminometer for taking light readings of samples contained in sample testing devices, or probes, including the probe assembly of the present invention. In one embodiment, the instrument has a dark reading chamber with a hinged cover, or hinged cap, connected to an elevator mechanism. The configuration of the connection prevents the photon detector of the instrument from being exposed to external light, even when the hinged cover is open and a test device is being loaded in the chamber. This is very important for signal stability and to reduce increased background photon counts, which is a primary source of decreased system sensitivity. The hinged cover, a shutter member in the instrument, and the various components of the elevator mechanism, cooperate to block the photon detector from exposure to external light as the elevator mechanism is depressed to lower the sample-containing device, or probe, into a reading position. Also, the elevator mechanism and shutter prevent the photon detector from being exposed to light even when the hinged cover is open and a test device is being loaded into the instrument. When the hinged cover is closed and the test device is lowered, a shaft rotates to open the shutter so a reading can be obtained in a previously photometrically stabilized dark environment.

In further embodiments, the instrument includes a communication port that allows the instrument to receive a signal from a measurement device in addition to the photon detector. The measurement device can be an external device or external sensing probe, capable of measuring or sensing a parameter other than that provided by the photon detector, such as, but not limited to, temperature, pH, dissolved gases, conductivity, reduction potential, and specific ions. The external probe can also be a multi-parametric probe capable of measuring or sensing more than one type of parameter. In some embodiments, the measurement device is internal to a housing of the instrument, at least in part, wherein the communication port for communicating with the measurement device can also be internal to the housing of the instrument.

As to the probe assembly, in one embodiment, it comprises a plunger that can be pressed downward to activate the probe assembly with only one hand. This forces sealed containment chambers in the probe onto a piercing tip, thereby puncturing the seals. One of the chambers contains a dry reagent and another contains a buffer solution. When the chambers' seals are punctured, the contents of the chambers mix to form a reagent solution. The reagent solution flows through a channel and through a sample containing swab tip, causing sample to be released into the reagent. The reagent then reacts with the sample and emits light proportional to the level of environmental contamination, by, but not limited to, such materials as ATP, ADP or alkaline phosphatase in the sample, and the reagent chosen for the particular application. The probe assembly can be directly inserted into the instrument to measure light emitted from the sample.

DETAILED DESCRIPTION OF THE INVENTION

The present invention relates to various embodiments of apparatus and methods for monitoring or measuring parameters of a sample of a product, ingredient, process, or environment that can be used to provide critical information that facilitates environmental and process quality in areas such as water treatment, holding, containment and disposal systems. These settings include, but ate not limited to, testing in the food, pharmaceutical, cosmetic, and medical industries. These settings may further include environmental conditioning and control equipment for general usage such as, but not limited to, commercial air conditioning equipment and cooling towers. Additional settings include sensitive environments potentially susceptible to malicious or inadvertent contamination with biological materials, such as military installations, hospitals or enclosed high occupancy buildings.

Drawings depicting certain embodiments of the invention are provided for purposes of illustration. Also, the invention is described in a context including the monitoring of pathogenic contamination by measuring light emission from a reaction. However, as one skilled in the art will appreciate, various aspects of the invention may also be applicable in a variety of other settings. Also, as will be appreciated, equivalent modifications can be made to the invention without deviating from the scope or spirit of the invention. Not all such possible modifications have been illustrated or described in order to avoid unnecessary detail that would obscure the description of the invention.

Figure 1A:
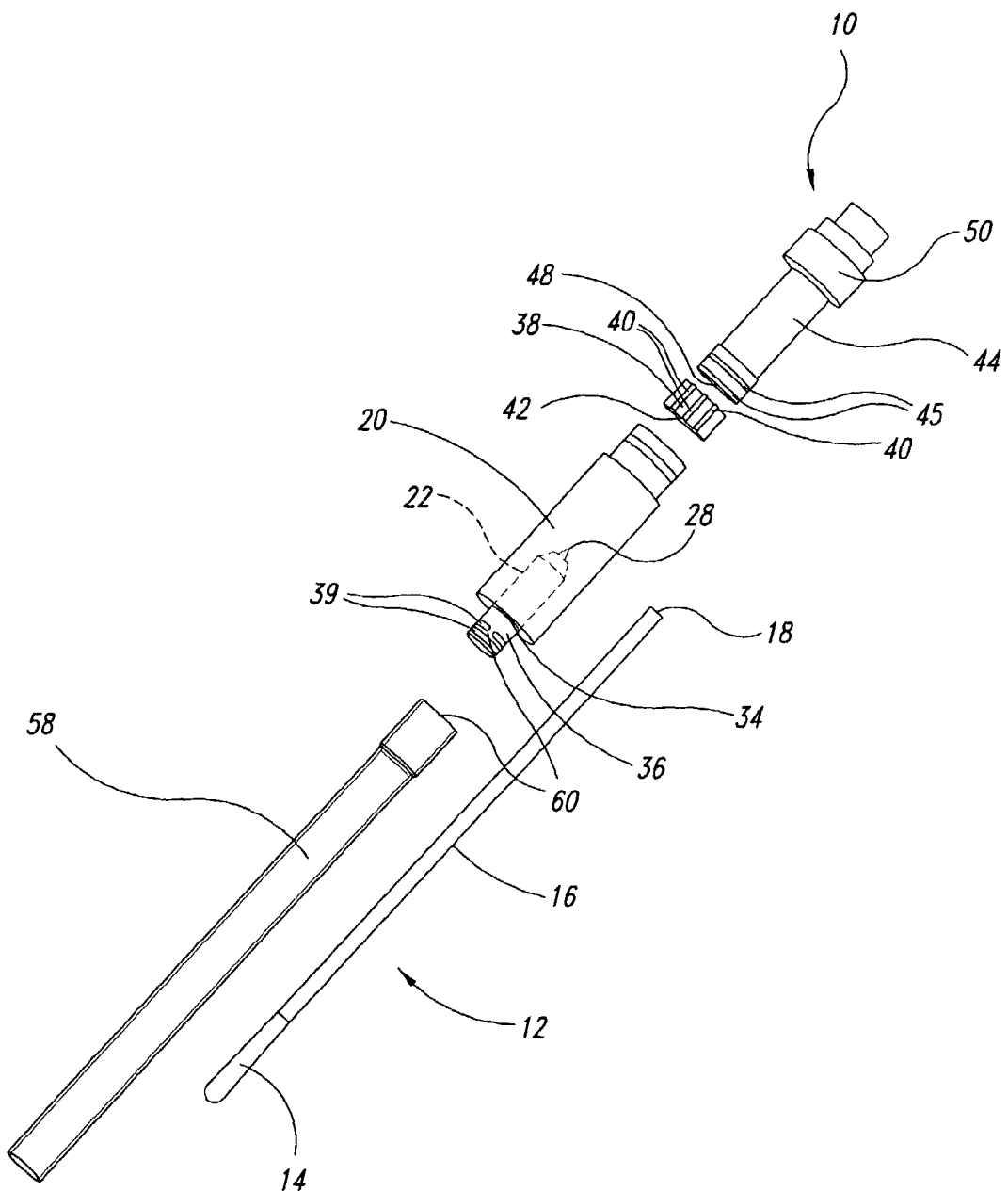
FIG. 1A is an exploded perspective view of a probe assembly according to one particular embodiment of the invention, also showing the connection tube in the interior of the probe housing, in dotted line.
Figure 1B:
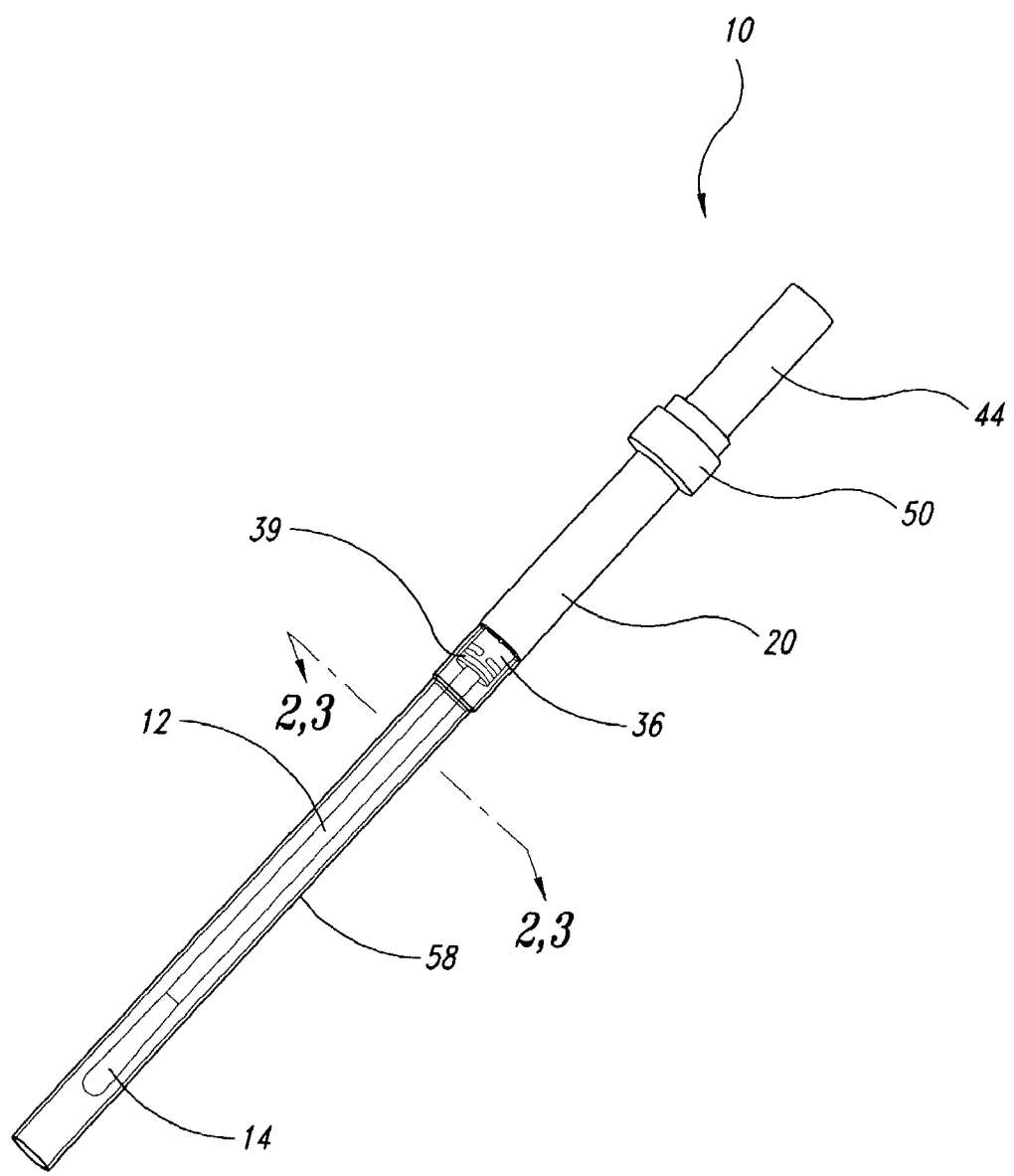
FIG. 1B is a perspective view of the probe assembly of FIG. 1.
Figure 2:
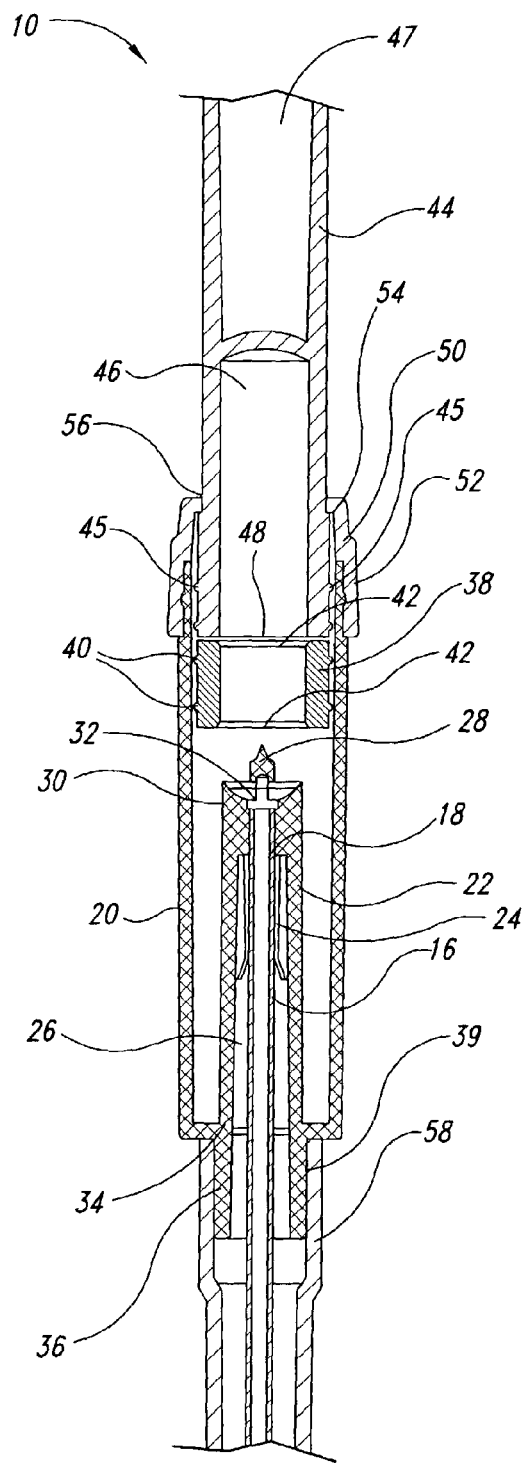
FIG. 2 is a diametric cross-sectional view of a portion of the probe assembly of FIG. 1 with the plunger in an "up" position.

FIGS. 1A, 1B, and 2 show an embodiment of a probe assembly 10 (sample testing device) of the present invention. FIG. 1A is an exploded view and FIG. 2 is a partial cross-sectional view of the probe assembly 10. The probe assembly 10 is used to collect sample and also serves as a reaction chamber in which the sample is released into a reagent solution. The probe assembly 10 can also serve as a device to retain sample while a parameter thereof is being measured by an instrument, such as the instrument 100 of the present invention. FIGS. 5–11 show an embodiment of the instrument 100 and a photon detection assembly 70 contained therein, that can be used to measure a parameter (i.e. photon count) of a sample contained in the probe assembly 10.

The probe assembly 10 includes a sample collection member, or swab stick 12, with a hollow shaft 16, as shown in FIG. 2. The swab stick 12 has a sample collection surface, or a swab tip 14. In the illustrated embodiment, the swab shaft 16, of the swab stick 12, is tubular. Also, the downward end ("upward" and "downward" being in reference to the orientation of the devices in the Figures) of the shaft 16 is open ended exposing the hollow interior of the tubular shaft 16. The swab tip 14 covers the downward open end. In most embodiments, the swab tip 14 is made of liquid permeable material, such as cotton, Dacron, poly-foam or porous liquid permeable plastic sampling surfaces to permit a reagent solution used with the probe assembly 10 to flow out of the hollow interior of the shaft 16 and through the swab tip 14 material, to react with sample collected on the swab tip 14. An upward end 18 of the swab stick 12 is secured to the rest of the probe assembly 10 by being inserted in a connection tube 22 as best seen in FIG. 2 and described below. In some embodiments, the swab tip 14 is pre-moistened to aid in sample collection. In other embodiments, a dry swab tip 14 is sufficient.

FIGS. 1A and 2 show that the probe assembly 10 has a probe housing 20 and a connection tube 22 formed within the probe housing 20. The connection tube 22 has an upward end portion 30 within the probe housing 20 and a downward end portion 34 joined to a downward end portion of the probe housing 20, such as by being integrally formed therewith. This is best seen in FIG. 2.

The downward end portion 34 of the connection tube 22 can also be integrally formed with a tubular stub 36, the tubular stub and the connection tube 22 being co-axially aligned. The tubular stub 36 extends downward away from the downward end 34 of the connection tube 22 and probe housing 20. Also, test tube grip rings 39 can be formed on the exterior surface of the tubular stub 36, as best seen in FIG. 1A.

The connection tube 22 functions, in part, as a joining member to join the swab stick 12 to the probe housing. As illustrated in FIG. 2, a portion of an interior chamber 26 of the connection tube 22 is provided with gripping members 24. The upward end 18 of the swab shaft 16 is configured and sized so that it can be co-axially inserted into the interior chamber of the connection tube 22, through the downward end 34 thereof, and pushed into the portion of the chamber having the gripping members 24 to secure the swab stick 12 to the probe housing 20. Also, the interior chamber 26 of the connection tube 22 has a reduced diameter above the gripping members 24 to provide a seal between the swab shaft 16 and the connection tube 22.

In the embodiment shown, the upward end portion 30 of the connection tube 22 is formed with an orifice 32. In some embodiments, the orifice has a smaller diameter than the average diameter of the interior chamber 26 of the connection tube. The orifice 32 provides an opening between the interior chamber 26 of the connection tube 22 and the exterior of the connection tube. The orifice 32 is centered on the top of the upward end portion 30 of the connection tube 22 with an opening facing upward. As can be seen in FIG. 2, a piercing tip 28 is also connected to the upward end portion 30 of the connection tube 22. In some embodiments, the piercing tip 28 is disposed directly above the orifice 32 by being formed on projection members that are joined at one end to the connection tube 22, with the other ends thereof extending over the orifice whereupon the piercing tip 28 is formed.

The probe assembly 10 has a plunger 44, or displacement member, that is slideably connected to the probe housing 20 and can be actuated, or pushed, to activate the probe assembly 10. See FIGS. 1A and 2. The plunger 44 has a liquid chamber 46. In one embodiment, the liquid chamber 46 contains a liquid buffer and detergent, and the liquid is sealed in the liquid chamber 46 by a foil seal 48 at the downward end of the plunger 44. In other embodiments, the liquid chamber may contain different reagents. The plunger 44 also has a hollow retaining cavity 47 that opens upward and can be used to retain the probe assembly in position by an instrument with a pin that is inserted in the cavity.

Figure 3:
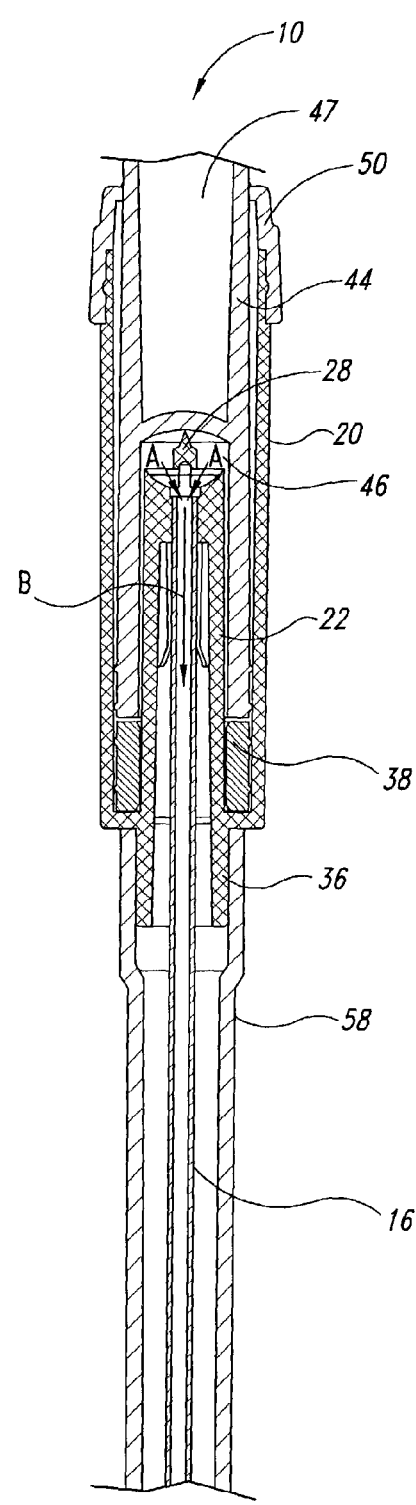
FIG. 3 is a diametric cross-sectional view of a portion of the probe assembly of FIG. 1 with the plunger in a "down" position.

As best seen in FIGS. 2 and 3, the plunger 44 can be in an "up" position, prior to activation of the probe assembly, wherein no reaction has yet occurred in the probe assembly 10, or pushed downward to a "down" position. When the plunger is pushed downward, or actuated, to the "down" position, the piercing tip 28 pierces the foil seal 48 of the liquid chamber 46 as well as foil seals 42 of a dry chamber 38, containing reagent, disposed below the plunger 44. It is also noted that the plunger 44 has seal rings 45 that mate with the interior surface of the probe housing 20 to prevent liquid, released from the liquid chamber, from leaking past the plunger 44 to the exterior of the probe assembly 10.

The dry reagent chamber 38, which may contain one or more reagents and desiccant, is disposed within the probe housing 20, under the plunger 44. The dry chamber 38 has foil seals 42 to seal the top and bottom of the chamber 38, with reagent sealed therewithin. There may be one or more positioners 40 longitudinally formed on the exterior surface of the dry chamber 38. The positioners 40 may, for example, take the form of ribs. See FIG. 1A. The positioners 40 are configured to engage the interior surface of the probe housing 20 and retain the dry chamber 38 in position above the piercing tip 28 while the plunger 44 is in the "up" position, but to permit the dry chamber 38 to slide downward past the piercing tip 28 when the plunger 44 is being displaced to the "down" position, thus breaking the foil seals 42.

In some embodiments, the dry chamber 38 and the liquid chamber 46 may be reversed in position. That is, chamber 46 may hold dry reagent, or a component of a reagent, and chamber 38 may hold a liquid reagent, or liquid component of a reagent. In other embodiments, both chambers may contain liquids. Furthermore, the components of a reagent solution that is selected for a particular application may be distributed throughout the chambers 38, 46 in various ways. For example, one chamber can contain a medium or buffering solution while the other contains a reacting reagent to facilitate energy emission from the sample. Also, some embodiments of the invention can comprise one chamber or more than two chambers. In a further embodiment, one chamber may contain a growth promotion medium and another may contain a stabilization or transport medium.

These may be used together or separately.

An annular cap 50 is fitted over the probe housing 20 and plunger 44. As best seen in FIG. 2, a lower portion 52 of the cap is configured to mate with the exterior surface of the probe housing 20 at the upper end of the housing and an upper portion 54 of the cap 50 mates with the exterior surface of the plunger 44. The plunger 44 is slidable in relation to the cap 50 while the probe housing 20 is securely mated to the cap 50. Also, there are small restriction devices 56 associated with the surface of the plunger 44 and engage the upper end of the cap 50 to hold the plunger 44 in the "up" position until a user activates the probe by depressing the plunger 44.

A translucent test tube 58 is provided for the probe assembly 10. The test tube 58 serves to protect the unused sampling device, to contain a sample containing device or to accumulate, activated sample and reagent, and as a measurement chamber. See FIGS. 1A, 1B and 2. When the probe assembly 10 is fully assembled and ready to activate, the test tube is fit over the swab stick 12 so that the swab tip 14 is contained within the test tube 58. See FIG. 1B. The diameter of an upper portion of the test tube 58 is sized to fit snugly over the test tube grip rings 39 on the tubular stub 36, such that when the test tube 58 is pushed over the tubular stub, a sufficiently tight fit is accomplished to securely couple the test tube 58 to the tubular stub 36.

As shown in FIG. 1A, there is also an atmospheric vent 60 comprised of a gaps in the grip protrusions 39 of the tubular stub 36 and upper edge of the test tube 58. This provides a vent to the atmosphere from the interior of the probe assembly 10, to release pressure buildup from the probe assembly when the plunger 44 is depressed. When the plunger 44 is depressed during activation of the probe, a pressure gradient is thus created between a high pressure point near the plunger 44, and a low pressure point at the atmospheric vent 60. This ensures that fluid flows from a point near the plunger 44 into the test tube 58.

Figure 1C:
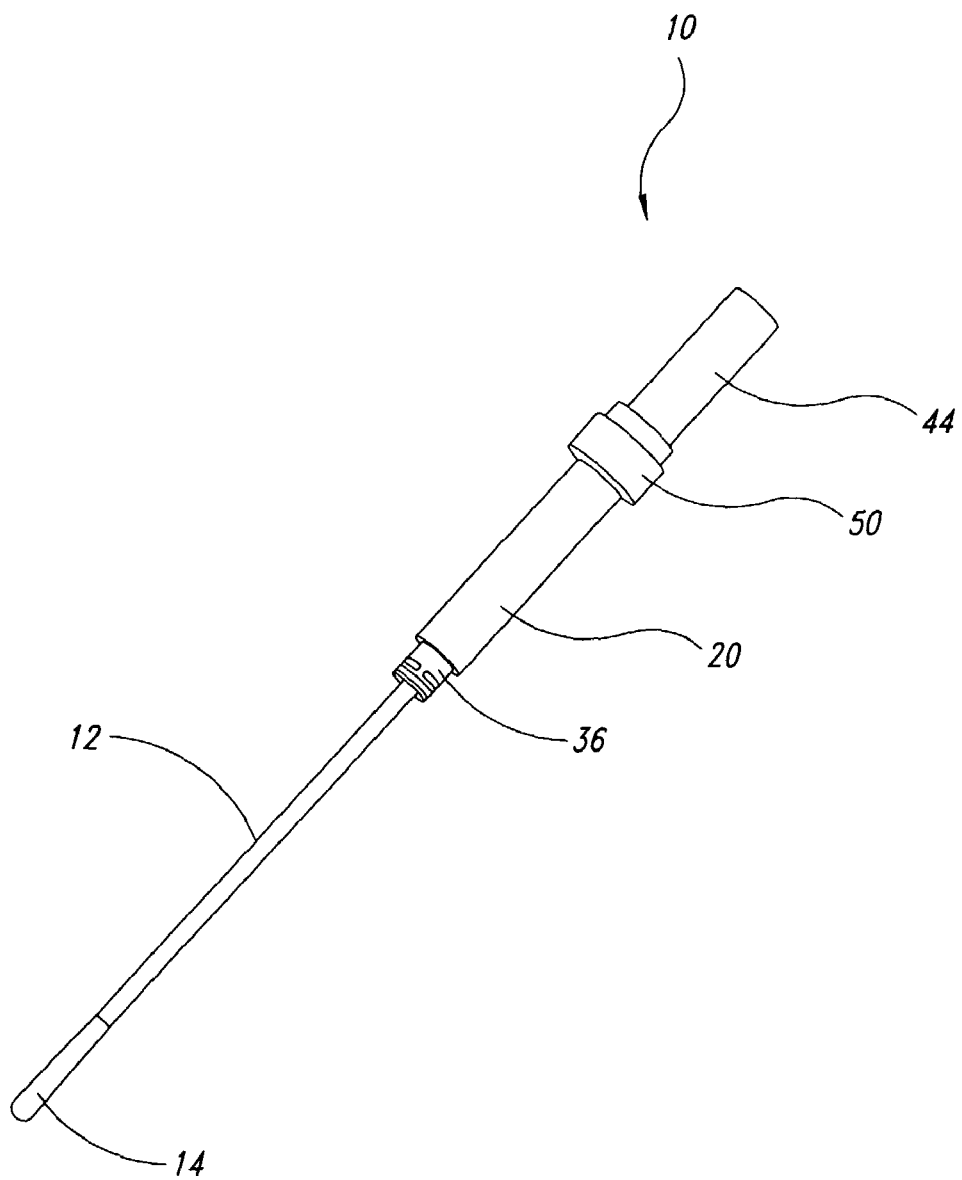
FIG. 1C is a perspective view of the probe assembly of FIG. 1 with the test tube removed.

In operation, the test tube 58 is removed from the probe, to expose the swab tip 14 for sample collection without removal from the connection Table 22, as shown in FIG. 1C. A user then uses the swab tip 14 to contact a sample surface. The test tube 58 is then replaced over the swab stick 12 and the upper end portion of the tube 58 is pushed over the tubular stub 36 to secure the test tube in place. To activate the probe, a downward force, sufficiently supplied by a user's hand or finger, is applied to the plunger 44 to drive it toward the piercing tip 28 thus breaking the foil seals 42, 48 of the dry chamber 38 and liquid chamber 46. The plunger 44 is displaced from the "up" position to the "down" position, as shown in FIGS. 2 and 3. The liquid buffer solution from the liquid chamber 46 and the reagent from the dry chamber 38 are released and mix. The reagent solution is forced through the orifice 32 at the upward end portion 30 of the connection tube, into the hollow shaft 16 of the swab stick 12 by the downward thrust of the plunger 44. The arrows labeled ("A") in FIG. 3 indicate one portion of the fluid flow path through the channel defined by the hollow shaft 16. The pressure build up created by the downward thrust of the plunger is released through the atmospheric vent 60, maintaining a pressure gradient that drives or propels the reagent solution downward through the flow path indicated by arrow ("B,") in the shaft 16 of the swab stick 12. The fluid exits the swab shaft 16 through the swab tip 14 thus contacting the collected sample and releasing some, or all, of the sample into the reagent solution. The reagent solution containing released sample then accumulates in the distal end of the test tube 58.

The distal end of the test tube serves as a measurement portion of the probe assembly 10 that, in some embodiments of the invention, is exposed to a photon detection device. The reagent and the sample react to produce light proportional to the amount of ATP, ADP, alkaline phosphatase or other suitable analyte in the sample. The instrument 100, which includes a photon detection device, such as the detection assembly 70 described below and illustrated in FIGS. 4–10, is used to measure light emitted from the reagent solution to provide an indication of level of contamination in the environment sampled. The configuration of the probe assembly 10, with the plunger 44, orifice 32, and fluid channels formed in part by the swab shaft 16, ensure that displacement of the plunger drives substantially all, or a sufficient amount of the reagent solution and sample into the measurement portion of the probe (distal end of the test tube 58) without the need for further action, such as shaking.

The following provides a summary of some of the features of the probe assembly 10 that contribute to precision, accuracy, reliability, and ease-of-use of various embodiments of the present invention. For example, the seals 42, 48 on the dry chamber 38 and liquid chamber 46, are not contacted by the swab tip 14 during activation of the probe assembly 10. This is in contrast to certain devices currently available that require the swab to be used to pierce membranes of reagent chambers. This present invention thus prevents sample from being removed from the swab tip 14 due to contact with the seals of the reagent chambers. Also, the probe assembly 10 of the invention is easy to activate with only one hand, by depressing the plunger 44. It also does not require shaking to mix the reagent with the liquid buffer solution as it is sufficiently mixed by the geometry of the probe assembly 10. For example, the reagent solution is adequately mixed by the release of the liquid and reagent, combined with the turbulent flow of the mixture through the orifice 32, and into and through the swab shaft 16, or channel, and through the swab tip 14. The amount of reagent is automatically, precisely, and accurately provided and dispensed by using only one hand to activate the probe. Also, in one embodiment, the probe assembly 10 is configured so that the swab tip 14 is above the bottom portion of the test tube 58 that is placed in the reading area of a photon detection device, or the photon sensing path. This can be seen in FIG. 9, wherein the circular opening 96 (a shutter 82 opening) approximates the photon sensing path of the photon detection device. Note that the swab tip 14 is just above this reading area. At the same time, the probe assembly 10 is configured to dispense a sufficient amount of liquid so that the liquid level 98 in the test tube 58 is nonetheless high enough to maintain liquid contact, or communication, with the swab tip 14. This can also be seen in FIG. 9. This configuration permits a photon detection device to measure light emitted from the solution with minimal interference from the swab tip 14, while the liquid is still able to liberate sample from the swab tip 14. The probe assembly 10 is also designed to eliminate reagent leakage, which decreases measurement precision and can contaminate the sampled surface, due to the various seals described above.

The method by which the probe assembly 10 is operated, fully integrates the operations of piercing barriers between separate reagent compartments, mixing said reagents, and dispensing with precision, known amounts of said mixed reagents, and finally, releasing the sample containing material for detection. The integrated piercing, transferring and channeling mechanism which sequentially performs the steps of activation, mixing and dispensing of all reagents through the sampling device avoids piercing reagent separation barriers with the sample containing surface, and resultant loss of sample on barrier debris, loss of reagent materials in voids or open cavities of the device, and requiring the operator to shake, screw or repetitively manipulate the device to ensure proper operation. It is also noted that the test tube 58, or measurement chamber, forms a continuous collection and reading chamber that is optically uniform and conducive to efficiency photometric measurement. This enhances photon transmission for more accurate, precise, and sensitive readings.

Figure 11:
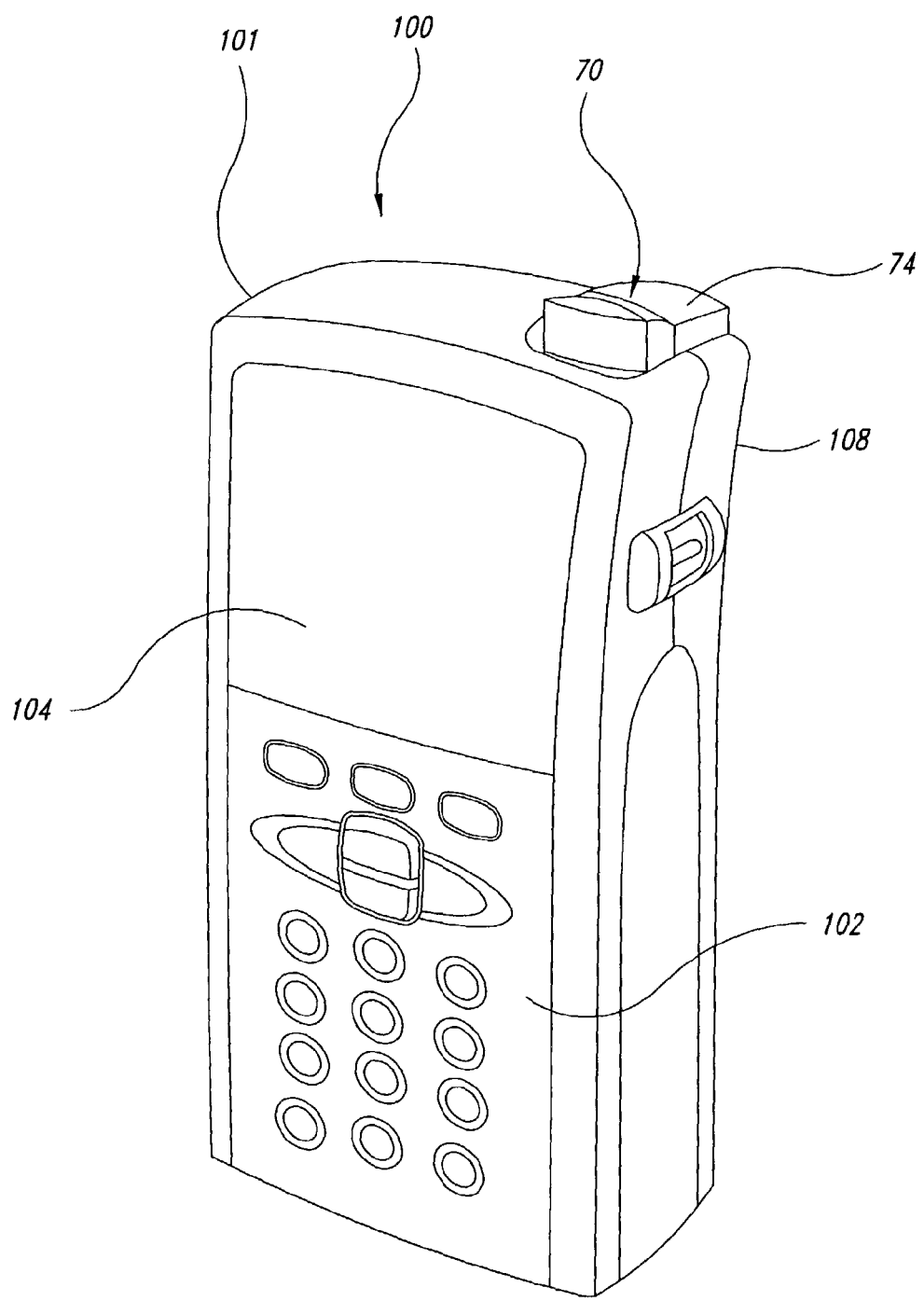
FIG. 11 is a perspective view of a measurement instrument according to one particular embodiment of the present invention, with the slidable shaft of the detection assembly in the "down" position.
Figure 12:
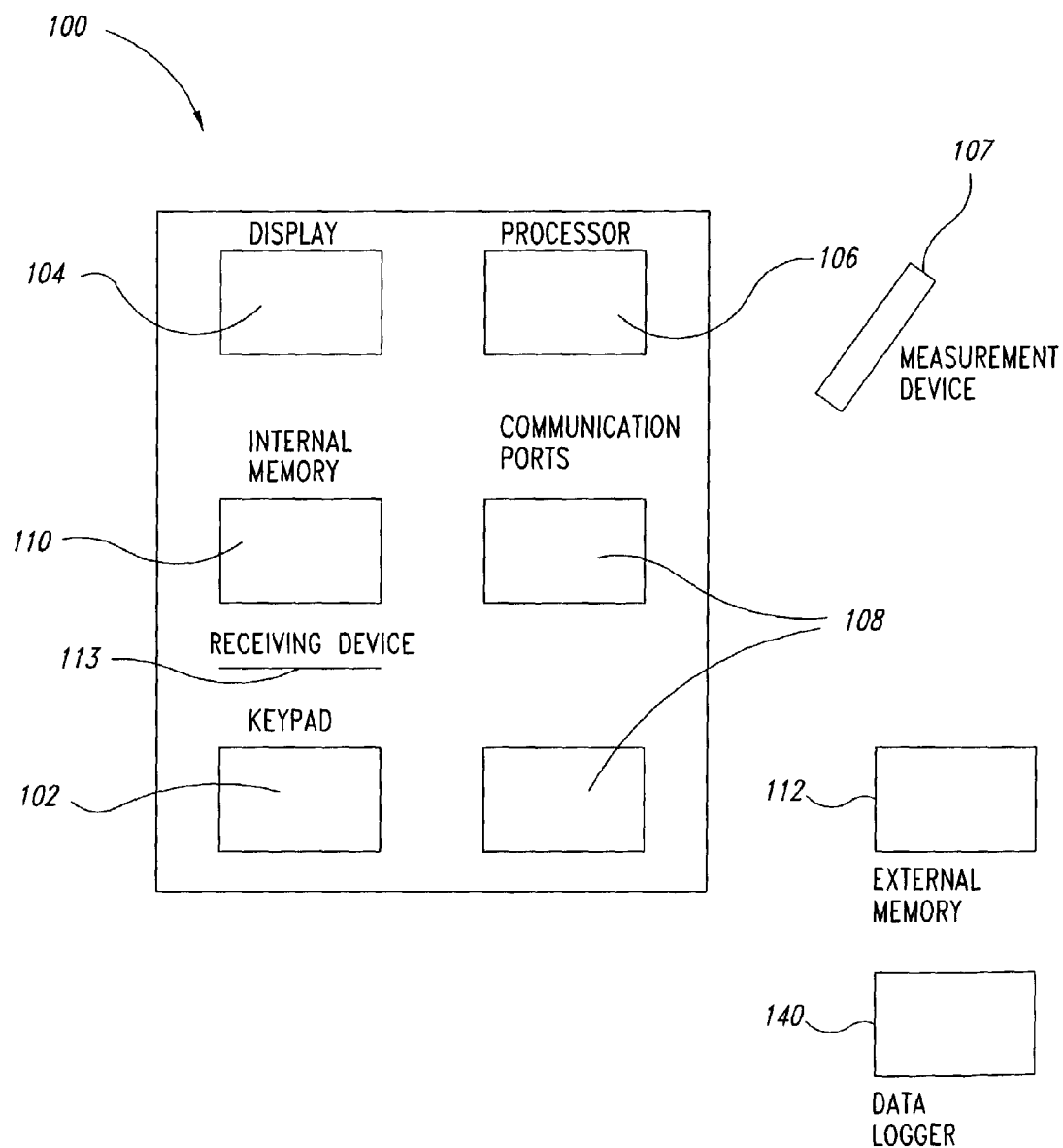
FIG. 12 is a simplified block diagram schematically illustrating one embodiment of the measurement instrument, without the sample testing device or photon detection assembly being shown.

Certain embodiments of the instrument 100 of the present invention comprise an instrument housing 101, within which the photon detection assembly 70 is contained. See FIGS. 11 and 12. FIG. 11 is an isometric view of the exterior of an embodiment of the instrument 100 with the instrument housing 101 shown and FIG. 12 is a block diagram of an embodiment of the instrument 100, showing an external measurement device 107 (a multi-parametric external probe is represented by the embodiment illustrated in FIG. 12), but without the photon detection assembly 70 or probe assembly 10 (sample testing device) being shown. Said external measurement device may be fixed or detachable from instrument 100 without impacting it's functionality. In FIG. 11 a top portion of the photon detection assembly 70 can be seen, with the rest of the detection assembly contained in the instrument housing 101.

The instrument 100 can include a key pad 102, or control panel, a display screen 104, a processor 106, and one or more communication ports 108. The communication ports 108 can comprise any variety of input and/or output devices, either internal to the instrument or external, for use either with measurement devices 107, or other external devices. In other embodiments, the instrument also comprises an internal system memory 110. In yet another embodiment, the instrument comprises a receiving device 113 for receiving and reading external memory devices 112, such as, but not limited to, memory cards and CD-ROM disks. In addition, other forms of external memory can be used with the instrument 100 by transferring data to or from the external memory through the communication ports 108. These other forms of external memory can comprise hard disks on general purpose computer systems 120 (described below), data loggers 140, or other types of remote databases 136.

The instrument 100 can be configured to receive signals from both a photon detection device of the photon detection assembly 70, which includes a photomultiplier tube, photodiode or other photon sensing detector, and other measurement devices 107 that can communicate with the instrument 100 through the communication port 108 thereof. See FIG. 12. As described, the measurement devices 107 may be external to the instrument 100 or be an integral part thereof. Such measurement devices 107, include, but are not limited to, external single or multi-parametric probes for monitoring other parameters essential to environmental safety or HACCP (Hazard Analysis and Critical Control Point) principles, such as, but not limited to, pH, temperature, dissolved gases, conductivity, reduction potential, and specific ions. One example multi-parametric probe is a combined temperature and pH probe, capable of providing measurements for both parameters simultaneously, or separately. A variety of multi-parametric (as well as single parametric) probes are currently available and widely used and can include the ability to measure a number of the parameters listed. For example, combined temperature/pH probes are widely used, as well as probes able to measure more than two parameters.

One example is multi-parametric probes currently widely available and capable of measuring pH, conductivity, temperature, pressure, and dissolved gases. Although the measurement device 107 represented in FIG. 12 is a probe, a myriad of other measurement devices can be substituted therefor.

The embodiments of the instrument 100 described above combine the ability to accurately, precisely, and efficiently measure luminescence parameters (which are often selected as CCP indicators in HACCP plans) with the photon detection assembly 70, with the ability to measure, compile, and analyze other parameters in conjunction with the measured luminescence parameters, using the same instrument 100. These other parameters, not necessarily related to light emission, are often selected as indicators for the same or different CCPs for which the luminescence parameters serve as indicators, with all the parameters being critical to a HACCP plan. This combined functionality of the instrument 100 is unique and provides many significant advantages. The advantages are highly apparent for food and environmental control applications where HACCP based standards are prevalent and luminescence is very relevant, but the same or equivalent modifications of the instrument 100 can also be used in a variety of other settings to provide significant benefits.

As to the food industry, the significant need for the capabilities of the present invention arise, in part, from the need to comply with HACCP based standards or regulations. In order to do so, the food processor, or food manufacturer, must be able to identify (critical control points) CCPs. CCPs are points, steps, or procedures where some form of control can be applied and a food safety hazard can be prevented, eliminated, or reduced. The processor may need to measure a variety of parametric indicators for each CCP (e.g. time and temperature measurements to verify a cooking process), identify deviations, perform trend analysis of deviations, and document the data to show compliance with the HACCP requirements. In carrying out a HACCP plan, a food processor is currently likely to use many single-function monitors to take isolated measurements (e.g. a temperature probe, a pH meter, and a separate photon counter to measure bioluminescence of an activated sample) and then to enter the readings manually on different data collection sheets. Such collection procedures are tedious, inefficient, and highly subject to human error. A serious risk of loss of data integrity by willful or negligent action by those involved in the data collection exists with the current state-of-the-art. In addition, examination of the relationship of multiple parameters to the quality of the production environment is difficult. The present invention solves these problems, as is further illustrated by an example embodiment described below.

In one example embodiment of the invention, the instrument 100 comprises a photon detection assembly 70 with a photo multiplier tube (PMT) or photodiode and is capable of communicating with a multi-parametric probe (i.e. an external measurement device 107) for measuring temperature and pH of an environment from which the sample is taken. Each of the different parameters to be measured, photon count, pH, and temperature, are critical indicators for the same CCP (or different CCPs) in an HACCP plan.

In this example embodiment, a user can use the instrument to measure photon count of a sample, store the photon count measurement temporarily or permanently on the instrument 100, and then use the instrument 100 and the multi-parametric probe 107 to read and store either temperature or pH, or both, of the relevant environment. The measurements of the various parameters can be taken simultaneously or sequentially. The data representing all the different parameters measured can be simultaneously viewed and compared on the display screen 104 of the instrument 100, without having to switch between different data collection sheets, or any otherwise separate data format.

In a preferred embodiment, the data collected is randomly allocated to the data storage facility in a manner that optimizes the amount of data retained but with full flexibility by the operator to assign any amount of data storage independent to any parameter of interest. In a most preferred embodiment, all such data is retained in its designated location in such a manner that willful or negligent of the primary data is precluded.

Previously, a user would have had to separately take and record the photon count of a sample, and then the pH or temperature of the environment. These data were manually recorded or logged in independent unrelated instruments. In order to view or analyze the photon count data together with the temperature and pH data, the user would have had to import it all into a single format, possibly by manually copying or entering it into a common database if it were recorded on data collection sheets. By contrast, with the instrument 100, all of the data representing the different parameters, including photon count, is integrated by being collected, recorded, and displayed by one device.

In the example embodiment, software is provided on the instrument 100 to analyze the integrated data (photon count, temperature, and pH) to determine whether critical limits for a CCP have been reached that require corrective action to comply with the HACCP plan. The software is stored on the memory 110 and drives the processor 106 of the instrument 100. If the critical limit(s) is trend sensitive to a combined interaction of the three separate parameters, the measured data can be analyzed in connection with a previous trend stored on the memory 110 of the instrument 100. The software can also generate a display format on the display screen 104 conducive to quick assessment of the relevant CCP or other factor (e.g. trending the data and displaying it in a graph(s)). None of these capabilities is currently available with an instrument that also has the capacity to measure bioluminescent parameters.

As can be seen from the above example, certain embodiments of the instrument 100 efficiently combine information from several distinct but related parameters, which can include photon measurement, to provide a more comprehensive, integrated, and efficient evaluation of a CCP or groups of related CCPs, or any other environmental or process condition. A further benefit of the instrument is that measurement of multiple parameters utilizing one instrument eliminates the high cost of procuring several measuring instruments. An additional benefit is the elimination of the potential for description of data integrity during sampling, transport, transcription or analysis of CCP compliance to the AACCP Plan.

As will be appreciated by one skilled in the relevant art, various equivalent modifications can be made to the above example embodiment of the instrument 100 without deviating from the scope of the invention. Portions of the software or hardware, or the associated method steps for using the same, can be left out or combined differently, or various equivalent modifications of the same can be added. For example, a myriad of different external measurement devices 107 can be used in place of the temperature/pH probe, such devices comprising those being capable of measuring such parameters as dissolved gases, conductivity, reduction potential, and specific ions. The external measurement device 107 will be selecting depending on the application. Also, the integrated data could be exported to a general-purpose computer (described below), via the communication port(s) 108, for analysis with software, in place of, or in addition to, analysis within the instrument 100.

Figure 13:
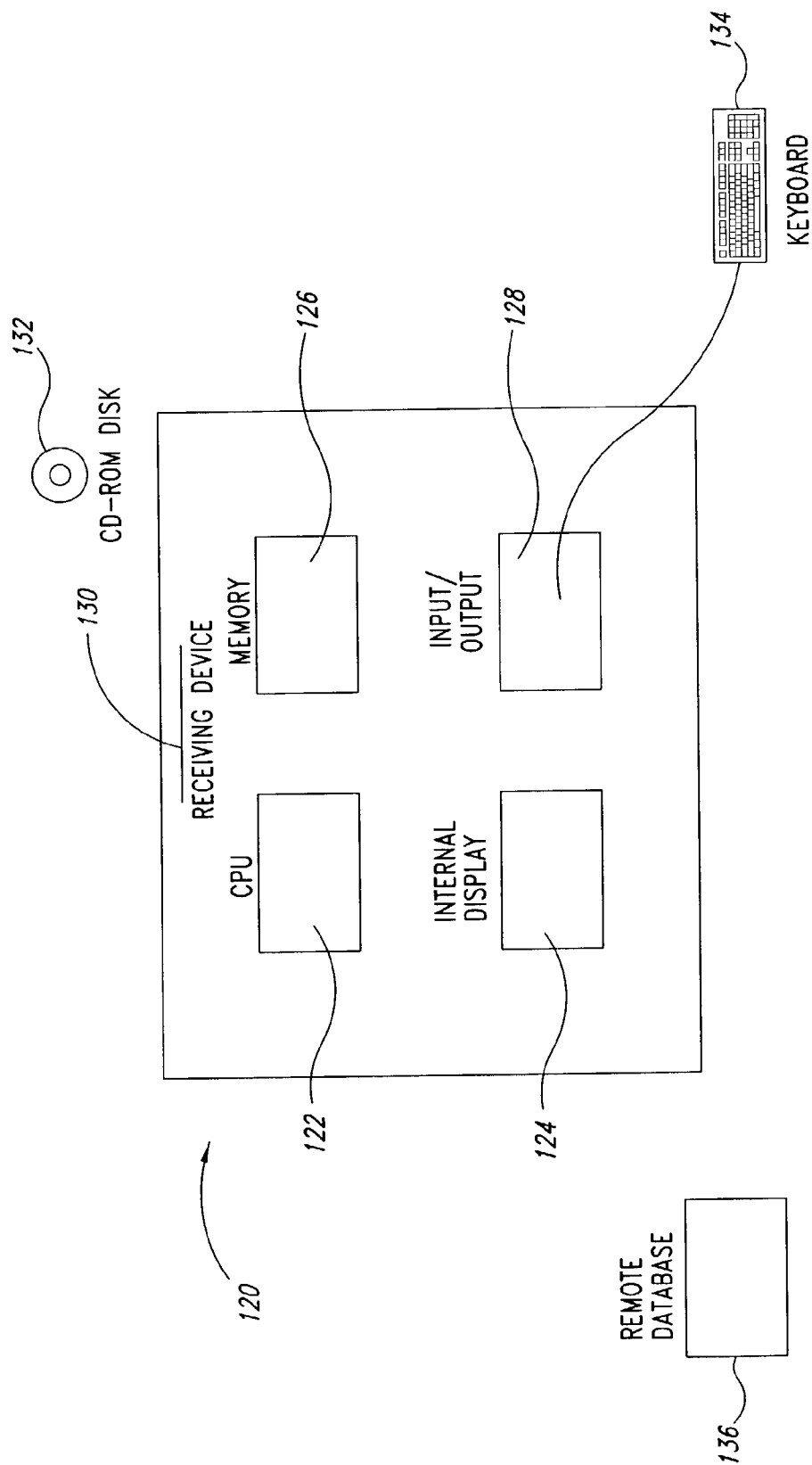
FIG. 13 is a simplified block diagram of a general purpose computer for use with various embodiments of the present invention.

The communication port 108 of the instrument 100 can provide for direct connection to a computer, a data transfer device, or other data analysis device for comprehensive data compilation and output. FIG. 13 is a block diagram of a general-purpose computer for use with some embodiments of the present invention. The computer system 120 includes a central processing unit (CPU) 122, a display screen 124, an internal system memory 126, and input/output devices 128. In addition, the computer 120 includes a receiving device 130 for receiving and reading computer-readable media 132, such as a diskette. Although the computer-readable media 132 is represented in FIG. 13 as a CD-ROM disk, the computer system 120 can employ other computer-readable media, including but not limited to, floppy disks, tape, flash memory, system memory 126, DVD-ROM, and hard drives. The input/output 128 can be connected to a variety of devices, including a keyboard 134, or remote or external database 136, or mouse (not shown). In addition, remote devices that send and receive signals can also communicate with the computer system 120 through these input/outputs 128, such as, but not limited to, other devices within a network, modems, data loggers 140, personal data devices, or palm pilots. Software used with the computer 120 to analyze data collected by the instrument 100 can include the capabilities of the software described above for the instrument 100. In addition, such software, like the software for the instrument 100, can also provide a myriad of other functions, such as, for example, being capable of assessing and monitoring compliance with the overall HACCP plan, or other quality control or safety program, such as a statistical process control program. Such software may be internal to instrument 100, external to instrument 100 or a combination of internal and external.

Figure 14:
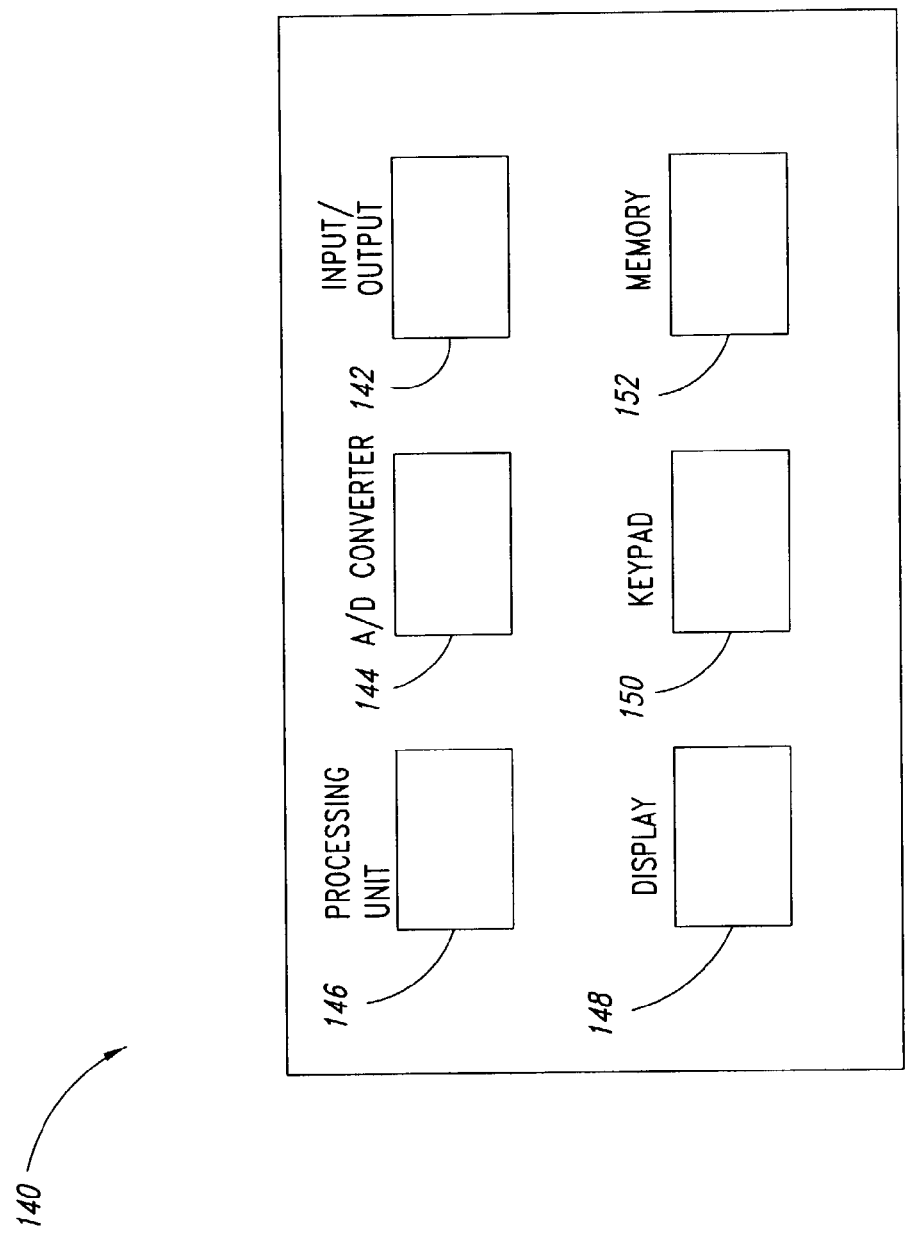
FIG. 14 is a simplified block diagram of a general purpose data logger or data transfer device for use with some embodiments of the present invention.

FIG. 14 is a simplified block diagram of a general purpose data logger 140 referenced above, that can be used to supply data or record data from a variety of sources, such as the instrument 100, measurement device 107, or the general purpose computer system 120. The embodiment illustrated in FIG. 14 comprises input and/or output devices 142, an analog to digital converter 144, a processing unit 146, a display 148, a keypad 150, and an internal memory 152.

Figure 4:
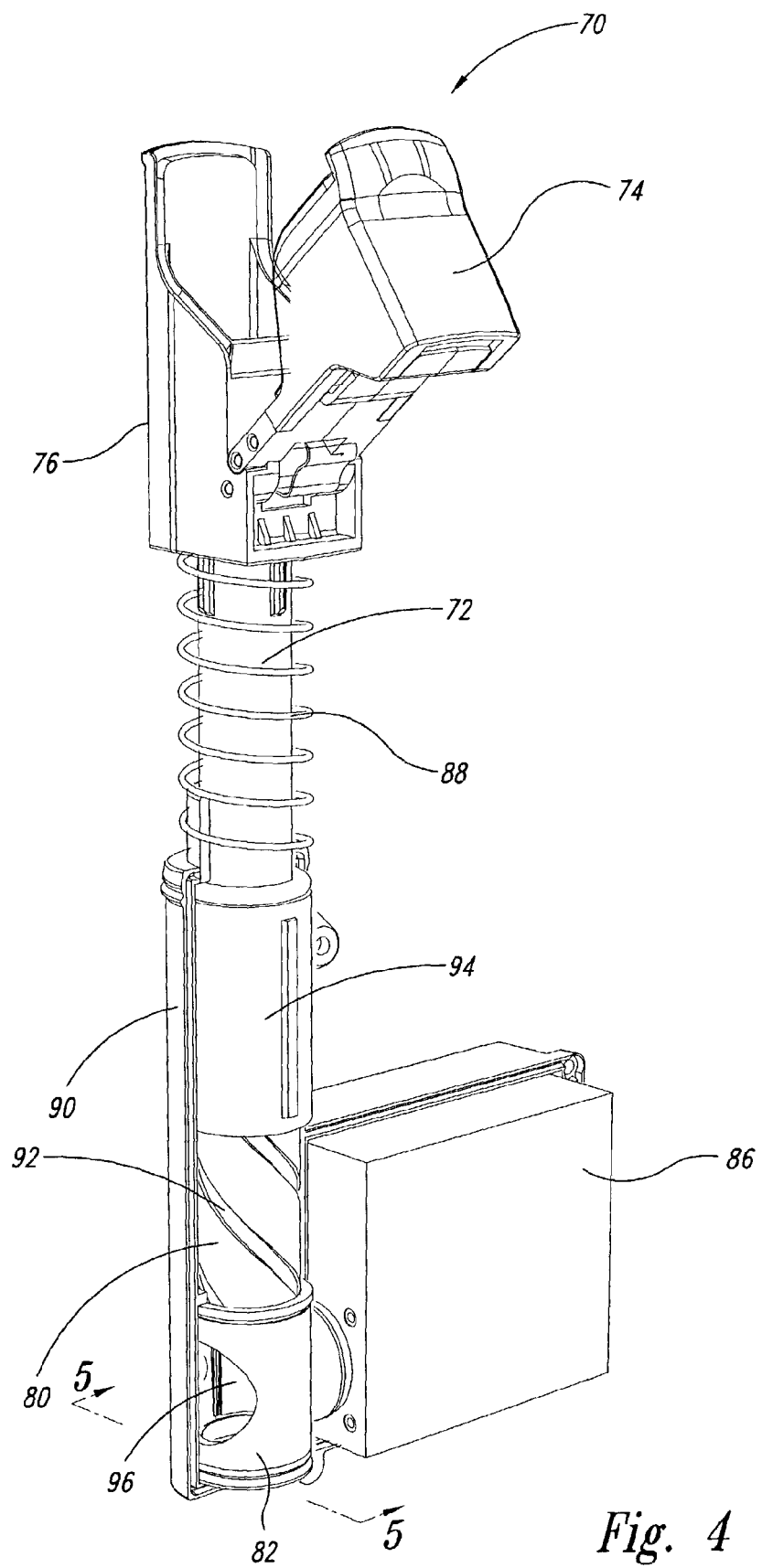
FIG. 4 is a perspective view of a detection assembly according to one particular embodiment of the invention with the slidable shaft in an "up" position and the hinged cover open.
Figure 5:
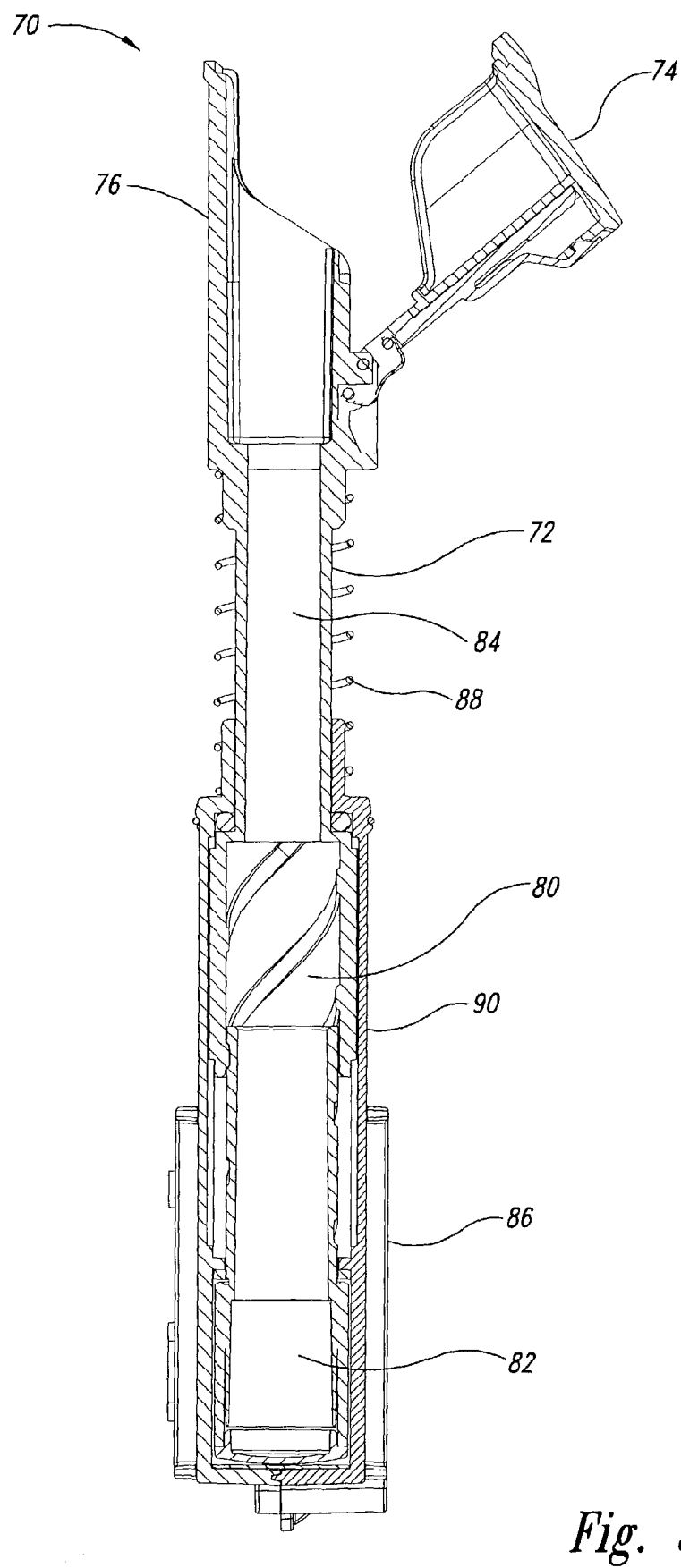
FIG. 5 is a cross-sectional view of the detection assembly of FIG. 4 as viewed from the side opposite the detector housing.

FIGS. 4 and 5 illustrate an embodiment of the instrument 100 comprising the photon detection assembly 70. The photon detection assembly 70 includes a slidable shaft 72, a rotatable member, or rotatable shaft 80, a holding member, or holding chamber 76, with a hinged cover 74, a shutter 82, and a detector housing 86 containing, in one embodiment, a photo-multiplier tube (PMT) or photo device for photon detection (the PMT is not shown).

The slidable shaft 72 has an interior chamber 84 configured to receive the probe assembly 10, or a similar device. When it is desired to measure light emitted from the activated probe assembly 10, it is inserted into the detection assembly 70 through the holding chamber 76, with a portion of the probe extending into the interior chamber 84 of the slidable shaft 72.

The holding chamber 76 is joined to the top portion of the slidable shaft 72. The hinged cover 74 is connected to the holding chamber 76 and is pivotable between an "open" and "closed" position. The hinged cover 74 is configured to prevent light from entering the interior chamber 84 of the slidable shaft 72 when it is adjusted to a "closed" position over the interior chamber 84. FIG. 4 shows the hinged cover open and FIG. 7 shows the hinged cover closed.

Figures 6A, 6B:
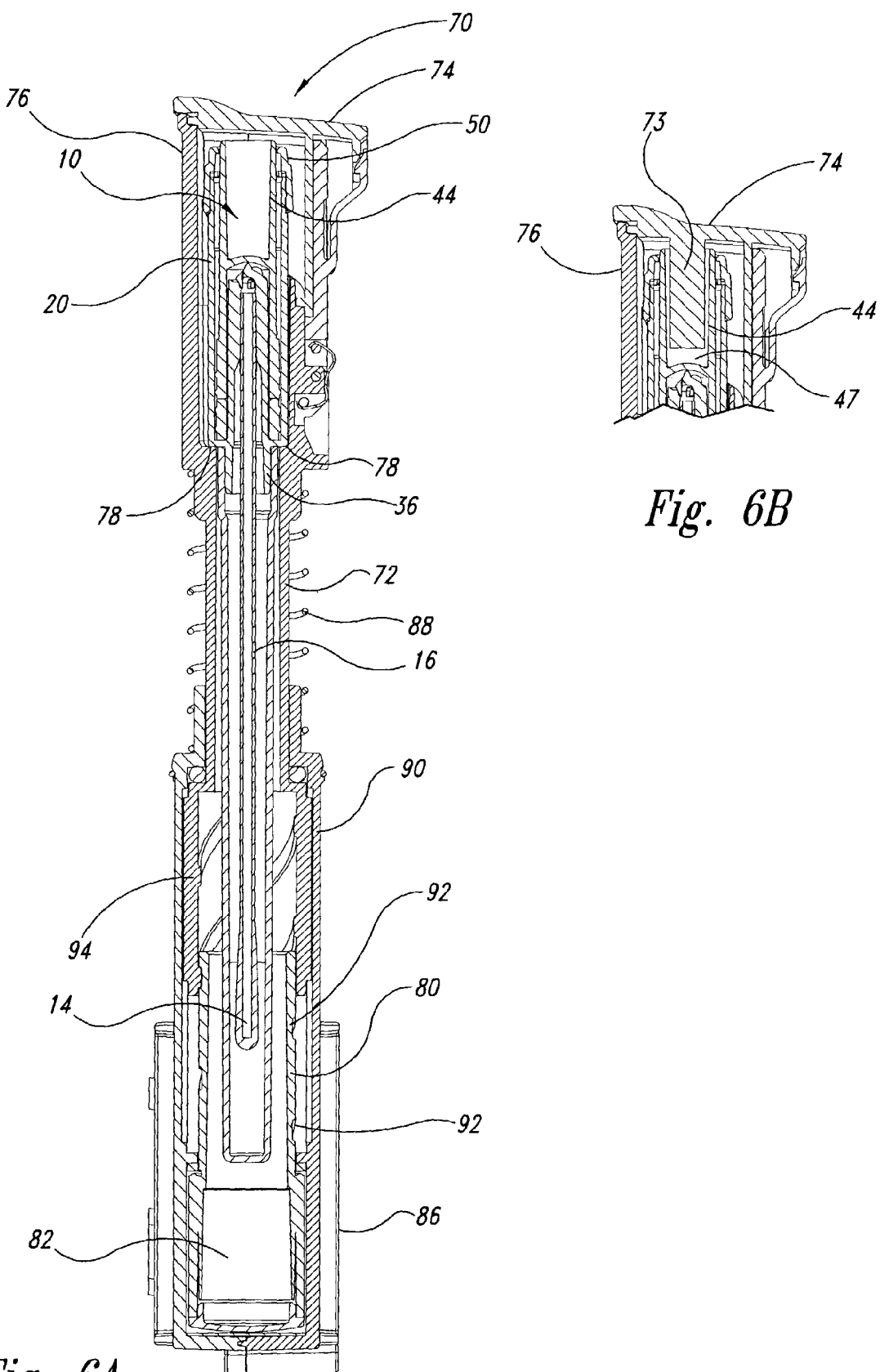
FIG. 6A is a cross-sectional view of the detection assembly of FIG. 7 with the slidable shaft in an "up" position with the hinged cover closed, and with the probe assembly activated and inserted in the detection assembly.
FIG. 6B is a diametric cross-sectional view of a portion of one embodiment of the detection assembly showing a positioning pin formed on a hinged cover of the detection assembly.

FIGS. 6A and 6B show the probe assembly 10 inserted in the slidable shaft 72 with the hinged cover 74 closed. As can be seen, the holding chamber 76 of the assembly 70 is configured to hold the plunger 44, probe housing 20, and cap 50 of the probe assembly 10. Near the bottom of the holding chamber 76, a substantially horizontal holding surface 78 extends inward from the interior wall of the chamber to mate against the bottom surface of the probe housing 20 surrounding the tubular stub 36. This holds the probe assembly 10 so that the test tube 58, and any sample contained therein, remains above the bottom of the detection assembly 70. In some embodiments the holding member, (or holding chamber 76) illustrated in FIGS. 6A and 6B is substituted with a holding chamber that can directly contain the sample rather than a portion of a testing device containing the sample. For example, the sample containing chamber can be within the holding chamber, or integral therewith.

Figure 7:
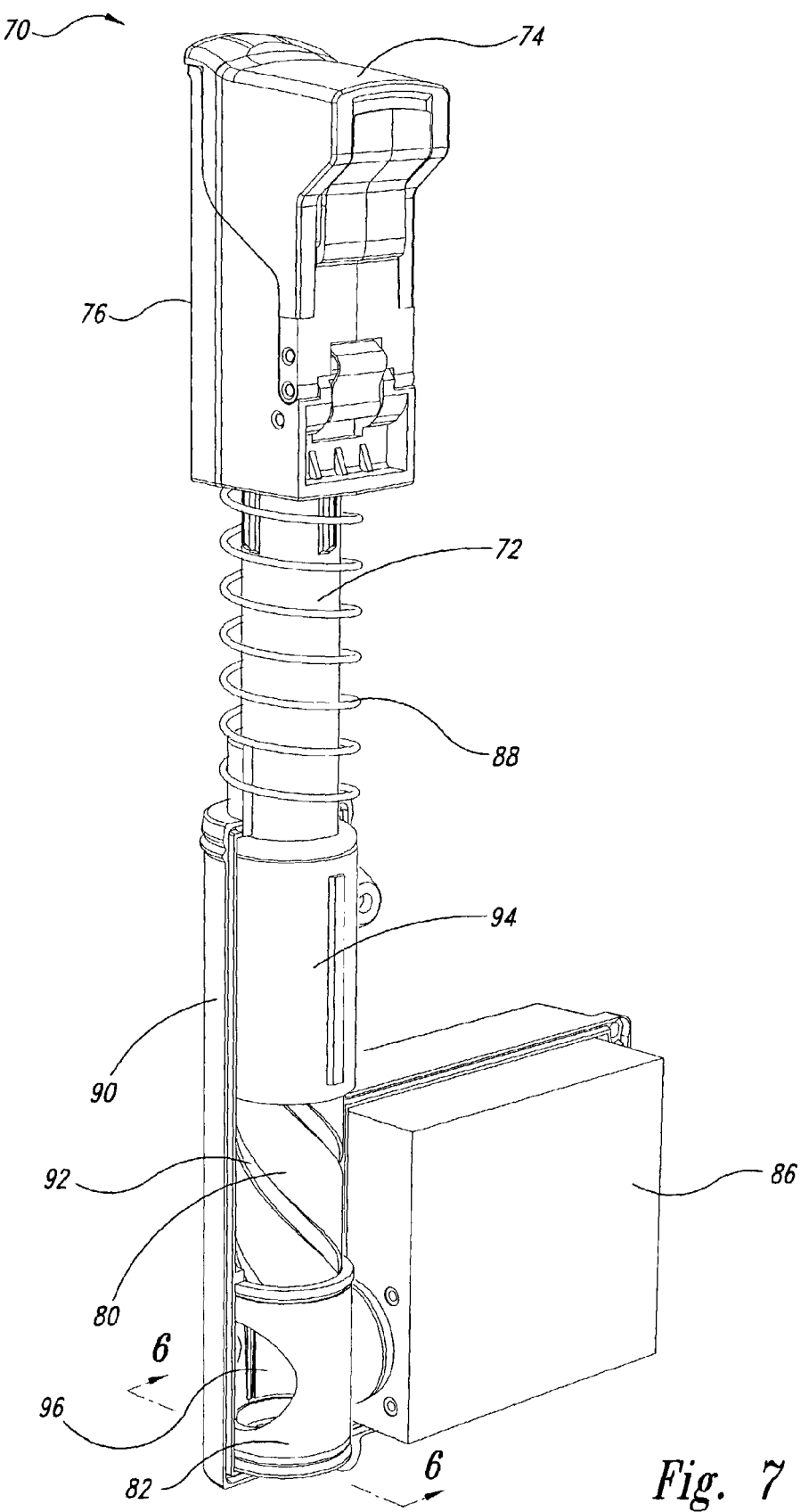
FIG. 7 is a perspective view of the detection assembly of FIG. 4 with the slidable shaft in an "up" position and the hinged cover closed.
Figure 8:
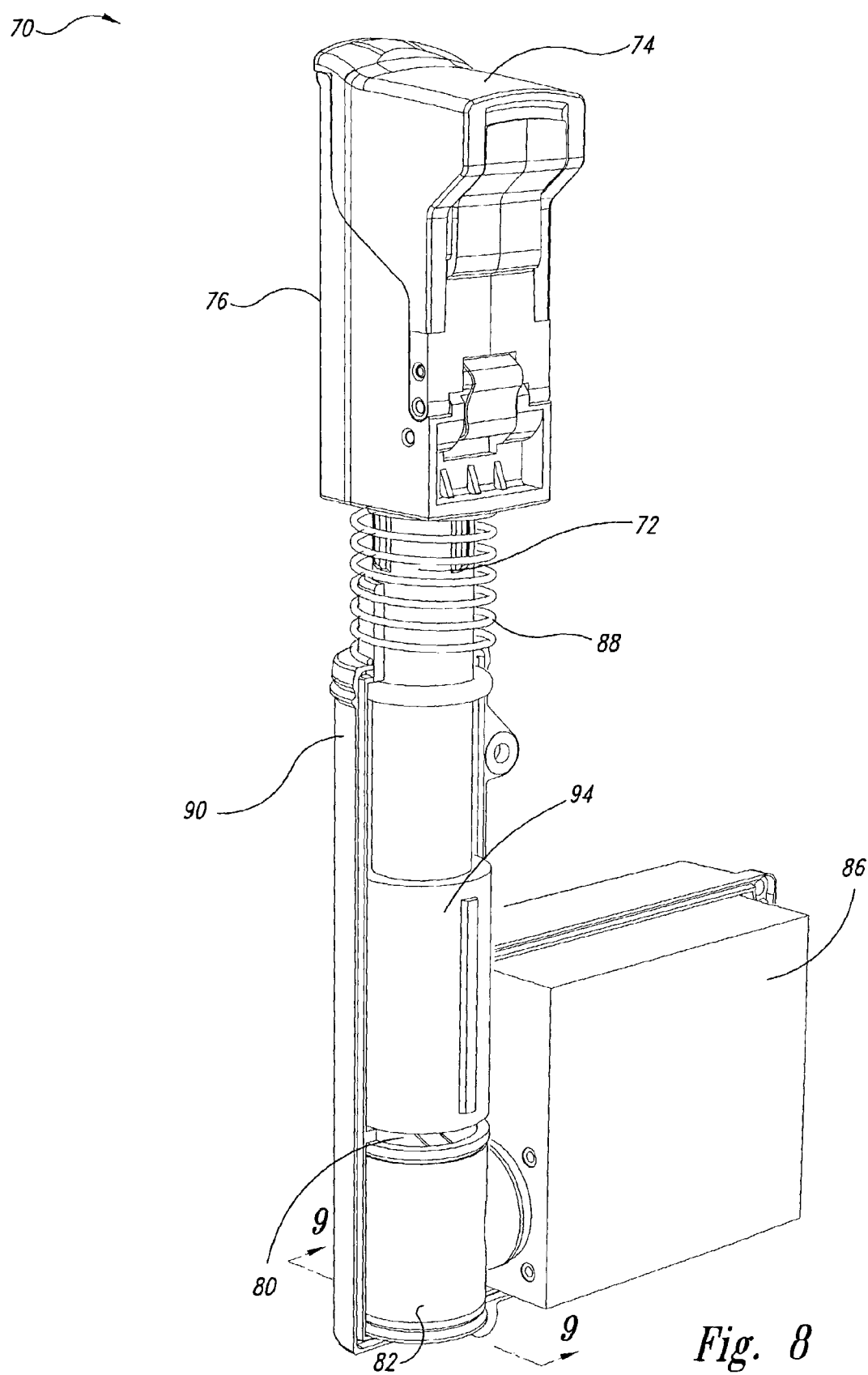
FIG. 8 is a perspective view of the detection assembly of FIG. 4 with the slidable shaft in the "down" position and the hinged cover closed.

As best seen in FIGS. 7 and 8, the slidable shaft 72 is vertically slidable in relation to a shaft housing 90. The shaft housing 90 and a coil spring 88 comprise an elevator mechanism for the shaft 72. The slidable shaft 72 and the shaft housing 90 are vertically and co-axially aligned. The bottom end of the coil spring 88 is set against the top end of the shaft housing 90 so that the coil spring 88 extends upward from the top of the shaft housing 90. The slidable shaft 72 is contained concentrically within the coil spring 88, with the upper end of the coil spring mated against the bottom of the exterior surface of the holding chamber 76. The slidable shaft 72, and the holding chamber 70 attached thereto, can be depressed from an "up" position to a "down" position, as shown in FIGS. 7 and 8. When in the "down" position shown in FIG. 8, the slidable shaft 72 can be locked in position using a releasable locking mechanism (not shown). When the locking mechanism is released, the coil spring 88 returns, or propels, the slidable shaft to the "up" position.

As shown in FIGS. 6 and 7, the rotatable shaft 80 is concentrically disposed within a cylindrical positioner 94 formed at the bottom portion of the slidable shaft 72. The exterior surface of the rotatable shaft 80 is lined with grooves 92 that form a downward cork screw or helical pattern on the rotatable shaft. The interior surface of the positioner 94 has guide members configured to fit within the grooves. The rotatable shaft 80 is free to rotate and is connected to the shutter 82, which rotates with the rotatable shaft. When slidable shaft 72 is vertically displaced, the positioner 94 is also vertically displaced, causing the guide members of the positioner to travel along the grooves. However, the positioner 94 is configured to travel vertically only, and does not rotate, and as such, causes the rotatable shaft 80 to rotate. In turn, the shutter 82 also rotates as it is coupled to the rotatable shaft and free to rotate with the shaft.

Figure 9:
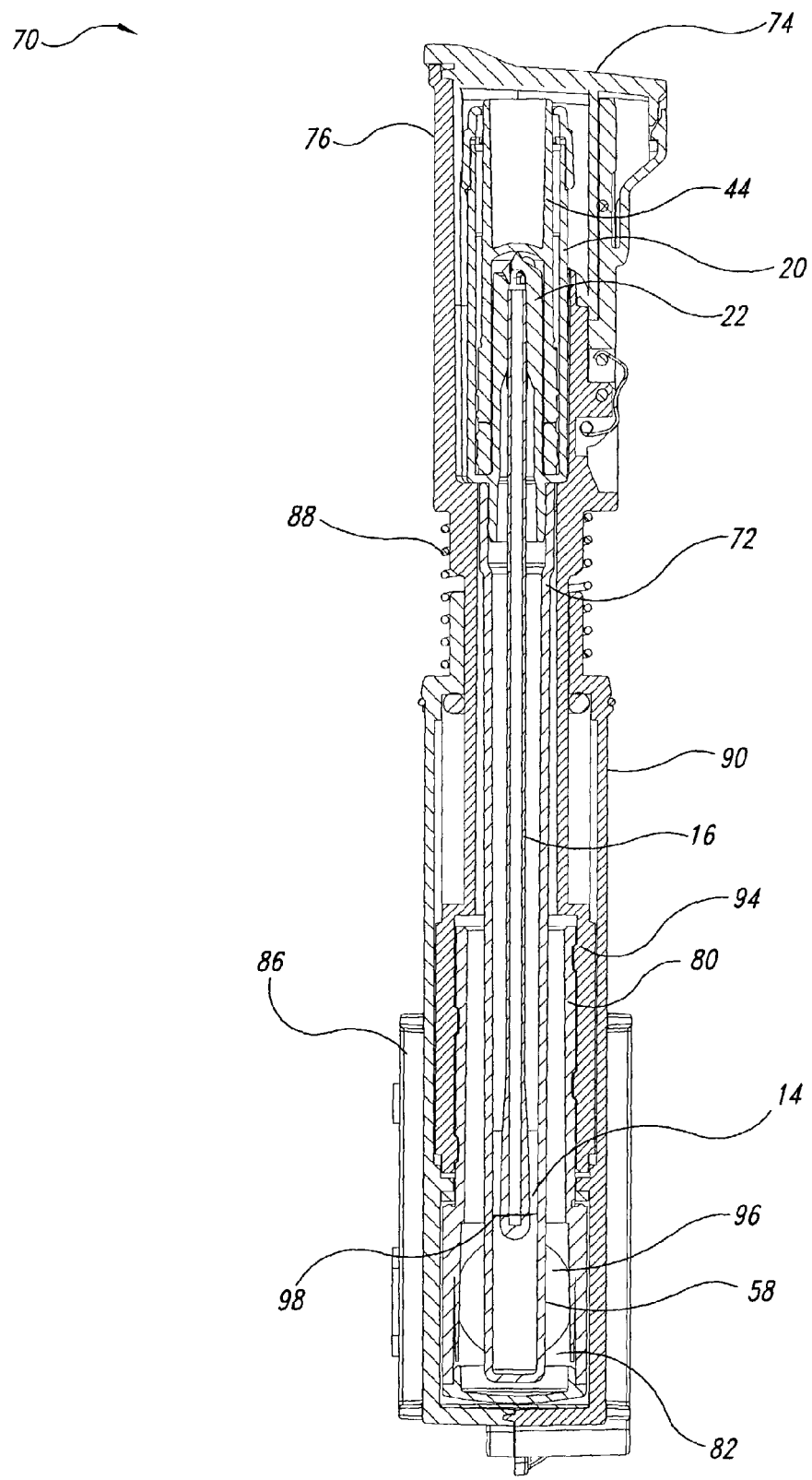
FIG. 9 is a cross-sectional view of the detection assembly of FIG. 8 with the slidable shaft in the "down" position and the hinged cover closed, and with the probe assembly activated and inserted in the detection assembly.
Figure 10:
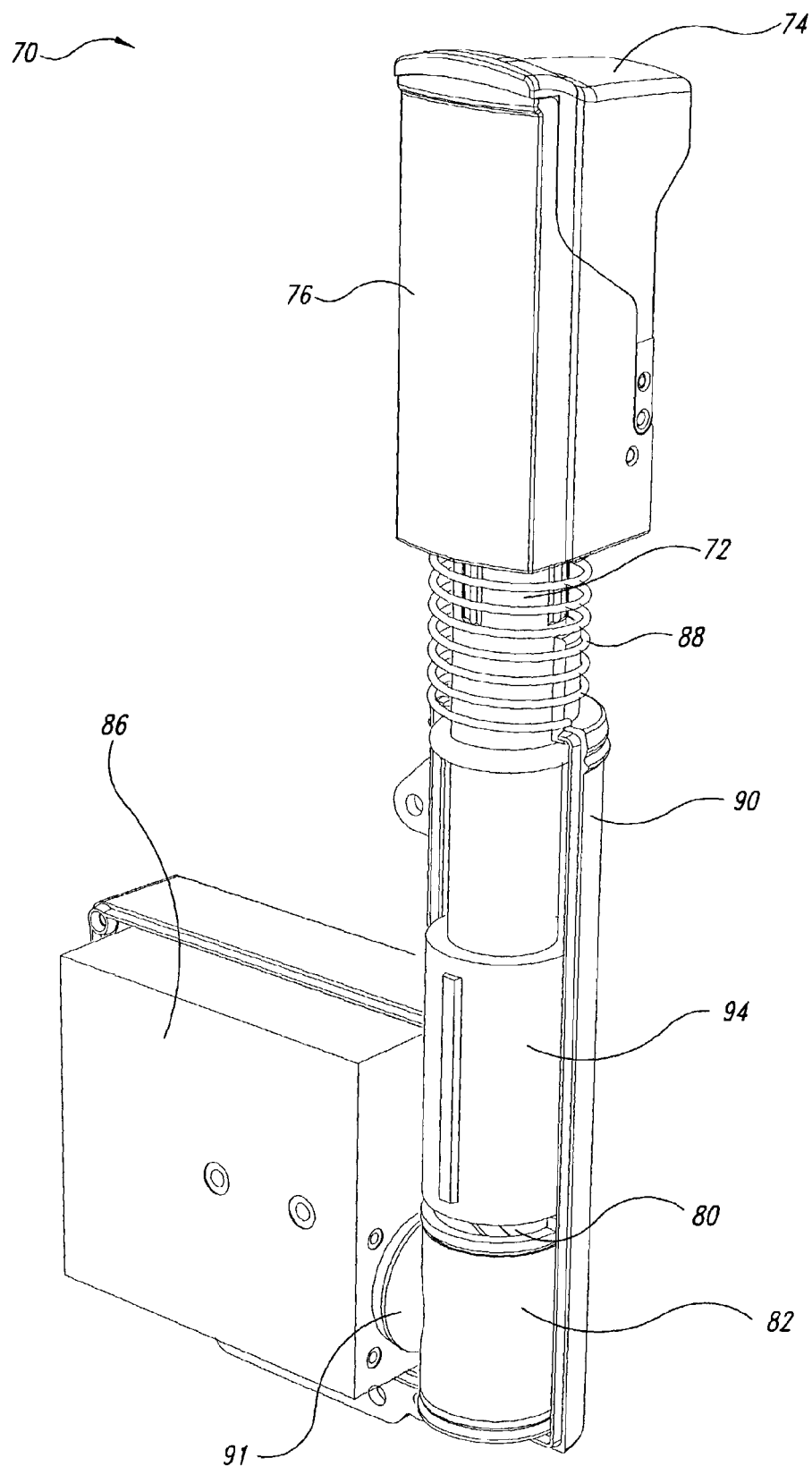
FIG. 10 is a rear perspective view of the detection assembly of FIG. 4, with the slidable shaft in the "down" position and the hinged cover closed.

In the embodiment illustrated in FIGS. 4 and 9, the shutter 82 is a cylindrically shaped member, adjacent the detector housing 86 containing the PMT. When the slidable shaft 72 is in the "up" position and the hinged cover 74 is open, as shown in FIG. 4, the shutter 82 is in a "closed" position, with an opening 96 of the shutter facing away from the detector housing 86. As such, the PMT is not exposed to external light entering from the open holding chamber 76, which could interfere with the precision and accuracy of the readings taken. The "up" position is a sample containing device loading position. When the slidable shaft 72 is displaced downward, the shutter rotates so that the opening 96 faces toward the detector housing 86 to permit a photon source in the detection assembly 70, such as a reacting sample in the probe assembly 10, to be detected by the photon detecting device. See FIG. 9. The "down" position is a sample measurement position. The detection assembly 70 thus provides a dark chamber 91 formed partially by the detector housing 86 and the shutter 82, that is photometrically stabilized prior to a reading (count), or measurement being taken, and also prevents external light from being detected by the photon detecting device during the reading. See FIG. 10.

It is also noted that the in some embodiments, the hinged cover 74 must be closed before the slidable shaft 72 can be displaced downward to the extent that the shutter 82 is open. This ensures that the photon detecting device is not exposed to external light. In one embodiment, as best seen in FIG. 11, the cover 74 is prevented from being opened by the instrument housing 101, when the slidable shaft 72 is in the "down" position.

During use, the locking mechanism for the slidable shaft 72 is released to allow the slidable shaft to be lifted into the "up" position by the coil spring 88, and the hinged cover 74 is opened, as shown in FIG. 4. An activated sample device, such as the probe assembly 10, is placed into the detection assembly and the hinged cover is closed. See FIGS. 6A and 6B. The slidable shaft 72 is then depressed to move the distal end of the test tube 58, in which the reacting sample is contained, into the detection, or measurement path of the photon detecting device. At the same time, the shutter 82 is rotated open to expose the reacting sample to the photon detecting device, as previously described. FIG. 9 shows the detection assembly in the "down" position with light from the reacting sample exposed to the photon detecting device. As can be seen, only the distal end of the test tube 58 containing the reacting sample is exposed through the opening 96 of the shutter 82. The swab tip 14 is maintained above the opening 96, but is still in contact with the liquid, having a liquid level 98. Again, as described earlier, this minimizes reading interferences from the swab tip 14, while maintaining the swab tip 14 in contact with the liquid to leech sample from the swab tip 14.

In another embodiment of the detection assembly 70, a positioning pin 73, or positioning member, in the hinged cover 74 mates with the retaining cavity 47 in the plunger 44 to align the probe assembly 10 in the dark chamber 91. See FIG. 6B. This helps to reproducibly position the probe in very close and exact proximity to the detector, but without the swab tip 14 being in the direct light measurement path and allows for the more accurate, sensitive readings compared to other available systems. Various embodiments of the hinged cover 74 can be constructed to permit the pin to engage the plunger 44 in this manner. For example, the hinged cover 74 could be independently slidable in relation to the holding chamber 76, in a vertical direction to raise the pin above the retaining cavity 47 before sliding the cap downward to engage the pin in the cavity 47.

As discussed previously, in some embodiments, the photon detection assembly 70 is contained within an instrument housing 101 of the instrument 100. FIG. 11 shows an embodiment of the instrument housing 101 containing the photon detection assembly 70, with the slidable shaft 72 in the "down" position for taking a reading of the sample. In this position, only the top of the photon detection assembly 70, comprising the hinged cover 74, is visible, with the rest of the detection assembly contained within the instrument housing.

Various reagents can be used with the embodiments of the invention. Some embodiments employ a reagent in dry form having a composition that enhances dissolution of a pellet upon device activation. Also, various liquids/solutions can be selected for use with the embodiments of the invention depending on the particular application and reagent used. The composition of the reagents and liquids are beyond the scope of this invention.

The various embodiments described above can be combined to provide further embodiments. All of the above U.S. patents, U.S. patent application publications, U.S. patent applications, foreign patents, foreign patent applications and non-patent publications referred to in this specification and/or listed in the Application Data Sheet, including but not limited to U.S. patent application Ser. No. 60/338,844, filed Dec. 6, 2001, and titled "SAMPLE COLLECTION AND TESTING SYSTEM" are incorporated herein by reference in their entirety. Aspects of the invention can be modified, if necessary, to employ systems, circuits and concepts of the various patents, applications and publications to provide yet further embodiments of the invention.

Although specific embodiments, and examples for the invention are described herein for illustrative purposes, various equivalent modifications can be made without departing from the spirit and scope of the invention, as will be recognized by those skilled in the relevant art. The teachings provided herein of the invention can be applied to wide variety of applications as noted. The various embodiments described can be combined to provide further embodiments. The described devices and methods can omit some elements or acts, can add other elements or acts, or can combine the elements or execute the acts in a different order than described, to achieve various advantages of the invention.

These and other changes can be made to the invention in light of the above detailed description. In general, in the following claims, the terms used should not be construed to limit the invention to the specific embodiments disclosed in the specification. Accordingly, the invention is not limited by the disclosure, but instead its scope is determined entirely by the following claims.

What is claimed is:

1. An instrument for use in monitoring a product, an ingredient, an environment or process, the instrument comprising:
   a photon detection assembly with a photon detector and a dark chamber;
   a communication port capable of receiving a signal from an additional measurement device other than the photon detector of the photon detection assembly, the signal corresponding to a parameter determined by the additional measurement device; and
   a processor operable to integrate the parameter with information received from the photon detector into integrated data.

2. The instrument of claim 1 wherein the additional measurement device is capable of measuring at least one of ATP level, ADP level, AMP level, alkaline phosphatase level, pH, temperature, dissolved gases, conductivity, microbiological count, and specific ions.

3. The instrument of claim 1 wherein the photon detector is a photon counter comprising a photo-multiplier tube or photodiode.

4. The instrument of claim 3 wherein the dark chamber has a shutter member rotatably positionable to be open or closed, a cylindrical holding member with a slidable shaft for positioning the sample and the shutter in close proximity to the detector when open, and a cover that opens to admit the sample but must be closed to measure the sample.

5. The instrument of claim 3 wherein the additional measurement device is an external probe, which may be fixed or removable from the instrument.

6. The instrument of claim 5 wherein the external probe is interchangeable with other external probes.

7. The instrument of claim 5 wherein the external probe is capable of measuring different parameters.

8. The instrument of claim 5 wherein the external probe is capable of measuring a single parameter different from the photon detector.

9. The instrument of claim 7 wherein the external probe is capable of measuring different parameters simultaneously.

10. The instrument of claim 7 wherein the different parameters include at least one of temperature, pH, dissolved gases, conductivity, and specific ions.

11. A monitoring instrument, comprising:
    a photon device;
    a reading chamber for retaining a light emitting sample to be analyzed using the photon device;
    a communication port that allows the instrument to receive a signal from an additional measurement device, the measurement device being capable of measuring a parameter other than photon count; and
    a processor operable to integrate the received parameter with information received from the photon device into integrated data.

12. The instrument of claim 11 wherein the additional measurement device comprises an external probe.

13. The instrument of claim 11 wherein the additional measurement device comprises an external probe which is capable of measuring at least one of temperature, pH, dissolved gases, conductivity, reduction potential, and specific ions.

14. The instrument of claim 12 wherein the external probe is capable of measuring a plurality of different parameters.

15. The instrument of claim 12 wherein the external probe is capable of measuring a single different parameter.

16. The instrument of claim 14 wherein at least one of the plurality of different parameters is temperature, pH, dissolved gases, conductivity, reduction potential, or specific ions.

17. The instrument of claim 11 wherein the communication port is capable of receiving signals from any of a plurality of interchangeable measurement devices.

18. The instrument of claim 17, wherein the plurality of interchangeable measurement devices comprise devices for measuring different parameters.

19. The instrument of claim 17 wherein the plurality of interchangeable measurement devices comprise an external probe, which may be fixed or detachable from the instrument.

20. The instrument of claim 17 wherein the plurality of interchangeable measurement devices comprise a plurality of external probes, with at least two of the external probes being capable of measuring different parameters.

21. The instrument of claim 20 wherein at least one of the external probes is capable of measuring temperature, pH, dissolved gases, conductivity, reduction potential, or specific ions.

22. The instrument of claim 11 wherein the instrument comprises a plurality of communication ports each capable of receiving a signal from a separate measurement device.

23. The instrument of claim 22 wherein at least one of the communication ports is capable of communicating with a general purpose computer.

24. The instrument of claim 23 wherein at least one of the communication ports is capable of communicating with a data logger.

25. The instrument of claim 23 wherein at least one of the communication ports is capable of communicating with an external memory system.

26. The instrument of claim 22 wherein at least two of the separate measurement devices measure different parameters.

27. The instrument of claim 26 wherein at least one of the separate measurement devices is an external probe.

28. The instrument of claim 27 wherein the external probe is capable of measuring temperature, pH, dissolved gases, conductivity, reduction potential, or specific ions.

29. A method of monitoring a sample of a product, an ingredient, a process, or an environment comprising:
provided an instrument having a photon detector and a communication port for communicating with a measurement device, the measurement device being capable of measuring a parameter in addition to a parameter measured by the photon detector;
providing the measurement device to be coupled to the instrument through the communication port;
collecting a sample from the environment, process, product or ingredient, and placing the sample in a chamber for analysis using the photon detector;
analyzing the sample using the photon detector;
measuring a parameter of the product, the ingredient, the environment or process using the measurement device;
communicating the parameter to the instrument via the communication port; and
integrating the received parameter with information received from the photon detector into integrated data.

30. The method of claim 29 wherein data received from the photon detector and the measurement device represents selected CCP indicators.

31. The method of claim 30 further comprising analyzing the data using a processor of the instrument to correlate to a CCP limit.

32. The method of claim 29 further comprising displaying data from the photon detector and the measurement device on a display device of the instrument.

33. The method of claim 32 further comprising displaying data from the instrument in graphical or chart form to facilitate data analysis, the display of that data and the analysis thereof being carried out by a processor of the instrument or an external processor.

34. The method of claim 29 further comprising recording data from the photon detector and the measurement device on a memory of the instrument.

35. The method of claim 29 further comprising recording data from the instrument in a random access configuration such that the user may allocate any amount of memory to each parameter being measured.

36. The method of claim 29 wherein the instrument comprises a plurality of communication ports and at least one of the communication ports is used to transfer data received from the photon detector and the measurement device to an external device.

37. The method of claim 35 wherein the external device comprises a processor used to analyze the recorded data.

38. The method of claim 36 wherein the external device is a general purpose computer.

39. The method of claim 36 wherein the external device comprises a data storage device.

40. The method of claim 39 wherein the external device is a general purpose computer and the data storage device is a hard disk coupled to the general purpose computer.

41. The method of claim 29 further comprising using a processor of the instrument to analyze data received from the photon detector and the measurement device.

42. The method of claim 41 wherein using the processor to analyze the data comprises providing software to be used with the instrument processor to indicate correlation with a CCP limit.

43. The method of claim 41 wherein the processor used to analyze the data may be internal to the instrument, external to the instrument, or any combination thereof.

44. The method of claim 29 wherein measuring a parameter of the process or environment using the instrument comprises providing a measurement proportional to at least one of ATP level, ADP level, alkaline phosphatase level, temperature, conductivity, pH, dissolved gases, specific ions, and microbiological count.

45. The instrument of claim 1, further comprising a memory wherein at least the integrated data is stored.

46. The instrument of claim 1, further comprising a display wherein at least the integrated data is displayed.

47. The instrument of claim 1, further comprising:
a memory wherein at least the integrated data and previous integrated data is stored; and
a display wherein at least the integrated data trended with the previous integrated data is displayed.

48. The instrument of claim 1, further comprising the additional measurement device wherein the parameter from the additional measurement device and the information received from the photon detector are concurrently collected.

49. The instrument of claim 1, further comprising a plurality of additional measurement devices wherein a plurality of parameters from the additional measurement devices and the information received from the photon detector are concurrently collected.

50. The instrument of claim 11, further comprising a memory wherein at least the integrated data is stored.

51. The instrument of claim 11, further comprising a display wherein at least the integrated data is displayed.

52. The instrument of claim 11, further comprising:
a memory wherein at least the integrated data and previous integrated data is stored; and
a display wherein at least the integrated data trended with the previous integrated data is displayed.

53. The instrument of claim 11, further comprising a second measurement device wherein a second parameter from the second measurement device, the information received from the photon device and the parameter received from the additional measurement device are integrated into the integrated data.

54. A method of sampling of a product, an ingredient, a process or environment using a sampling instrument, the method comprising:
analyzing a sample using a photon detector residing in the sampling instrument, the sample collected from the product, the ingredient, the process, or the environment;
receiving a signal from a measurement device, the measurement device being capable of measuring a parameter other than a photon count and the signal comprising information corresponding to the measured parameter;
integrating the information corresponding to the measured parameter with information received from the photon detector into integrated data; and
storing the integrated data into a memory residing in the sampling instrument.

55. The method of claim 54, further comprising measuring the parameter using the measurement device, wherein the measurement device resides in the sampling instrument.

56. The method of claim 54, further comprising:
measuring the parameter using the measurement device, wherein the measurement device is external to the sampling instrument; and
communicating the signal to the sampling instrument from the external measurement device.

57. The method of claim 54, further comprising:
measuring a second parameter using an external measurement device that is external to the sampling instrument;
communicating a second signal to the sampling instrument from the external measurement device, the second signal comprising information corresponding to the second parameter; and
integrating the information corresponding to the second parameter, the information received from the photon detector, and the information received from the measurement device into the integrated data.

58. The method of claim 54, further comprising displaying the integrated data on a display residing on the sampling instrument.

59. The method of claim 54, wherein data received from the photon detector and the measurement device represents selected CCP indicators.

60. The method of claim 54 further comprising analyzing the integrated data using a processor of the sampling instrument to correlate to a CCP limit.

61. The method of claim 54 wherein the received signal comprises at least one selected from a group consisting of a measurement proportional to at least one of an ATP level, an ADP level, an alkaline phosphatase level, a temperature, a conductivity, a pH, a dissolved gases, a specific ion, and a microbiological count.

* * * * *